US008349331B2

(12) United States Patent
Chuntharapai et al.

(10) Patent No.: US 8,349,331 B2
(45) Date of Patent: Jan. 8, 2013

(54) ANTI-INTERFERON-α ANTIBODIES

(75) Inventors: Anan Chuntharapai, South San Francisco, CA (US); Jin K. Kim, South San Francisco, CA (US); Leonard G. Presta, South San Francisco, CA (US); Timothy Stewart, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/034,551

(22) Filed: Feb. 24, 2011

(65) Prior Publication Data

US 2011/0206663 A1   Aug. 25, 2011

Related U.S. Application Data

(60) Division of application No. 11/423,588, filed on Jun. 12, 2006, now Pat. No. 7,910,707, which is a continuation of application No. 10/044,896, filed on Jan. 9, 2002, now Pat. No. 7,087,726.

(60) Provisional application No. 60/270,775, filed on Feb. 22, 2001.

(51) Int. Cl.
*A61K 39/395* (2006.01)
(52) U.S. Cl. ............... 424/145.1; 424/158.1; 424/178.1
(58) Field of Classification Search .................. None
See application file for complete search history.

(56) References Cited

U.S. PATENT DOCUMENTS

| | | | |
|---|---|---|---|
| 4,289,690 A | 9/1981 | Pestka et al. | |
| 4,341,761 A | 7/1982 | Ganfield | |
| 4,423,147 A | 12/1983 | Secher et al. | |
| 4,474,754 A | 10/1984 | Shimizu | |
| 4,514,507 A | 4/1985 | Secher | |
| 4,824,432 A | 4/1989 | Skurkovich et al. | |
| 4,885,166 A | 12/1989 | Meyer et al. | |
| 4,902,618 A | 2/1990 | Berg | |
| 4,973,556 A | 11/1990 | Bove et al. | |
| 5,055,289 A | 10/1991 | Frincke | |
| 5,071,761 A | 12/1991 | Meyer et al. | |
| 5,073,491 A | 12/1991 | Familletti | |
| 5,196,323 A | 3/1993 | Bodo et al. | |
| 5,240,864 A | 8/1993 | Koga | |
| 5,317,089 A | 5/1994 | Adolf | |
| 5,503,828 A | 4/1996 | Testa | |
| 5,516,515 A | 5/1996 | Vellucci et al. | |
| 5,626,843 A | 5/1997 | Skurkovich | |
| 5,676,942 A | 10/1997 | Testa | |
| 5,780,027 A | 7/1998 | Maroun | |
| 5,789,551 A | 8/1998 | Pestka | |
| 5,869,293 A | 2/1999 | Pestka | |
| 5,888,511 A | 3/1999 | Skurkovich | |
| 5,919,453 A | 7/1999 | Benoit et al. | |
| 6,001,589 A | 12/1999 | Pestka | |
| 6,117,423 A | 9/2000 | Berg | |
| 6,136,309 A | 10/2000 | Novick et al. | |
| 6,150,503 A | 11/2000 | Pestka | |
| 6,180,370 B1 | 1/2001 | Queen et al. | |
| 6,299,870 B1 | 10/2001 | Pestka | |
| 6,300,474 B1 | 10/2001 | Pestka | |
| 6,312,924 B1 | 11/2001 | Presnell | |
| 6,333,032 B1 | 12/2001 | Skurkovich | |
| 6,410,697 B1 | 6/2002 | Berg | |
| 6,433,145 B1 | 8/2002 | Lafleur | |
| 6,514,753 B1 | 2/2003 | Pestka | |
| 6,548,056 B2 | 4/2003 | Presnell | |
| 6,747,131 B1 | 6/2004 | Pestka | |
| 6,827,934 B1 | 12/2004 | Co et al. | |
| 2001/0012514 A1 | 8/2001 | Skurkovich | |
| 2002/0192748 A1 | 12/2002 | Ratelli | |
| 2003/0044410 A1 | 3/2003 | Skurkovich | |
| 2003/0138404 A1 | 7/2003 | Maroun | |
| 2003/0147581 A1 | 8/2003 | Doi | |
| 2003/0147889 A1 | 8/2003 | Tovey | |
| 2004/0067888 A1 | 4/2004 | Tovey | |
| 2004/0105841 A1 | 6/2004 | Pestka | |
| 2004/0110715 A1 | 6/2004 | Escary | |
| 2004/0126799 A1 | 7/2004 | Escary | |
| 2004/0132139 A1 | 7/2004 | Escary | |
| 2004/0142431 A1 | 7/2004 | Escary | |
| 2004/0203118 A1 | 10/2004 | Escary | |

FOREIGN PATENT DOCUMENTS

| | | |
|---|---|---|
| CA | 1306961 | 9/1992 |
| CZ | 267 392 B1 | 12/1990 |
| CZ | 276 203 B6 | 4/1992 |
| CZ | 276 204 B6 | 4/1992 |
| DE | 231007 | 12/1985 |
| DE | 254593 | 3/1988 |
| DE | 265291 | 3/1989 |
| DE | 277087 | 3/1990 |
| DE | 279266 | 5/1990 |
| DE | 279317 | 5/1990 |
| DE | 279546 | 6/1990 |
| DE | 279547 | 6/1990 |

(Continued)

OTHER PUBLICATIONS

Nguyen et al., Hepatology, vol. 35, p. 425-432, 2002.*
(International Search Report Dated Dec. 11, 2002).
Adolf et al., "Production of Monoclonal Antibodies to human IFN-α and Their Use for Analysis of the Antigenic Composition of Various Natural Interferon" *Journal of Cellular Physiology Supplement* 2:61-68 (1982).
Aguet et al., "A crystaline synthetic peptide representing the epitope of a monoclonal antibody raised against synthetic interferon-α 1 fragment 1 1 1-1 16" *European Journal of Biochemistry* 146:689-691 (1985).
Alexenko et al., "Mapping of an epitope of human leukocyte alpha interferon A which is recognized by the murine monoclonal antibody NK2" *Biomed Sci.* 2(4):403-409 (1991).

(Continued)

*Primary Examiner* — Yunsoo Kim
(74) *Attorney, Agent, or Firm* — Morrison & Foerster LLP

(57) ABSTRACT

The present invention relates generally to the generation and characterization of neutralizing anti-IFN-α monoclonal antibodies with broad reactivity against various IFN-α subtypes. The invention further relates to the use of such anti-IFN-α antibodies in the diagnosis and treatment of disorders associated with increased expression of IFN-α, in particular, autoimmune disorders such as insulin-dependent diabetes mellitus (IDDM) and systemic lupus erythematosus (SLE).

23 Claims, 8 Drawing Sheets

FOREIGN PATENT DOCUMENTS

| | | |
|---|---|---|
| DE | 279548 | 6/1990 |
| DE | 283154 | 10/1990 |
| DE | 4216200 | 11/1993 |
| EP | 0 091 543 | 10/1983 |
| EP | 0 119 476 | 2/1984 |
| EP | 0 139 676 B1 | 8/1984 |
| EP | 0 064 063 | 9/1985 |
| EP | 0 158 420 | 10/1985 |
| EP | 0 332 084 | 9/1989 |
| EP | 0 431 950 | 6/1991 |
| EP | 0 050 129 | 3/1992 |
| EP | 1 236 800 | 9/2002 |
| FR | 2657881 | 8/1991 |
| GB | 2 111 527 | 7/1983 |
| GB | 2 160 544 | 12/1985 |
| GB | 2 195 342 | 4/1988 |
| JP | 58035122 | 3/1983 |
| JP | 58035124 | 3/1983 |
| JP | 58225028 | 12/1983 |
| JP | 61013156 | 6/1984 |
| JP | 60065000 | 4/1985 |
| JP | 61072722 | 4/1986 |
| JP | 61099828 | 5/1986 |
| JP | 61225136 | 10/1986 |
| JP | 63142000 | 6/1988 |
| JP | 4077431 | 3/1992 |
| JP | 6050971 | 2/1994 |
| KR | 8801757 | 9/1988 |
| KR | 9200051 | 1/1992 |
| SU | 1756349 | 8/1992 |
| WO | WO 82/01773 | 5/1982 |
| WO | WO 83/00693 | 3/1983 |
| WO | WO 84/03106 | 8/1984 |
| WO | WO 84/03105 | 4/1988 |
| WO | 93/20187 | 10/1993 |
| WO | WO 95/13539 | 5/1995 |
| WO | 96/34096 | 10/1996 |
| WO | WO-97/29131 A1 | 8/1997 |
| WO | 97/41229 | 11/1997 |
| WO | WO 98/06431 | 2/1998 |
| WO | WO 98/28001 | 7/1998 |
| WO | WO 99/64440 | 12/1999 |
| WO | WO 99/64461 | 12/1999 |
| WO | WO 00/32223 | 6/2000 |
| WO | WO 01/54721 | 8/2001 |
| WO | WO 01/62287 | 8/2001 |

OTHER PUBLICATIONS

Alexenko et al., "Reconstruction of an epitope capable of binding murine monoclonal antibodies NK2 within the sequence of human leukocyte interferon alpha F by site-directed mutagenesis" *Biochem Biophys Res Commun.* 169(3):1061-1067 (Jun. 29, 1990).

Alexenko, et al., "The antiproliferative and Antiviral Activities of IFN-Γ Variants in Human Cells" *J. of Interferon and Cytokine Research* 17:767-779 (1997).

Alkan and Braun, "Epitope mapping of human recombinant interferon alpha molecules by monoclonal antibodies" *Synthetic peptides as antigens—Ciba Foundation Symposium 119* 119:264-278 (1986).

Allen, G., et al., "Analysis and Purification of Human Lymphoblastoid (Namalwa) Interferon Using a Monoclonal Antibody" *J. Gen. Virol.* 63:207-212 (1982).

Andersson et al., "Application of Four Anti-Human Interferon-α Monoclonal Antibodies for Immunoassay and Comparative Analysis of Natural Interferon Mixtures" *J. of Interferon Research* 11:53-60 (1991).

Anonymous, "Human Interferon Alpha Subtypes, URL: http://www.researchd.com/cytokines/ifnasubt.htm" *Diagnostic Research, Inc.* (retrieved on Nov. 25, 2002).

Ansell, P. R. J., "Hybridoma technology: a view from the patent arena" *Immunology Today* 21(8):357-358 (Aug. 2000).

Antalis et al., "The serine protease inhibitor (Serpin) plasminogen activation inhibitor type 2 protects against viral cytopathic effects by constitutive interferon α/β priming" *Journal of Experimental Medicine* 187:1799-1811 (1998).

Bach, J. F., "Insulin-Dependent Diabetes Melitus as an Autoimmune Disease" *Endocrine Reviews* 15(4):516-542 (1994).

Baldeon et al., "Interferon-α and interferon-γ differentially affect pancreatic β-cell phenotype and function" *American Physiological Society* 275:C25-C32 (1998).

Batteux et al., "FCγRII (CD32)-dependent induction of interferon-alpha by serum from patients with lupus erythematosus" *Eur. Cytokine Netw.* 10(4):509-514 (Dec. 1999).

Beilharz, M. W., "Therapeutic potential for orally administered type 1 interferons" *PSTT* 3(6):193-197 (Jun. 2000).

Berg, K., "Identification, Production, and Characterization of Murine Monoclonal Antibody (LO-22) Recognizing 12 Native Species of Human Alpha Interferon" *J. of Interferon Research* 4:481-491 (1984).

Blanco et al., "Induction of dendritic cell differentiation by IFN-alpha in systemic lupus erythematosus" *Science* 294(5546):1540-1543 (Nov. 16, 2001).

Bogdan, C., "The function of type I Interferons in antimicrobial immunity" *Current Opinion in Immunology* 12:419-424 (2000).

Borrebaech, C. A. K., "Antibodies in diagnostics from immunoassays to protein chips" *Immunology Today* 21(8):379-357 (Aug. 2000).

Brand et al., "Antibodies Developing Against a Single Recombinant Interferon Protein May Neutralize Many Other Interferon-/141 Subtypes" *J. of Interferon Research* 13:121-125 (1993).

Brod et al., "Ingested inteferon a suppresses Type I diagetes in non-obese mice" *Diabetologia* 41(10):1227-1232 (Sep. 1998).

Brod, S.A., "Autoimmunity Is a Type I Interferon-Deficiency Syndrome Corrected by Ingested Type I IFN via the GALT System" *J. of Interferon and Cytokine Research* 10:841-852 (1999).

Cai and Garen, "A melanoma-specific $V_H$ antibody cloned from a fusion phage library of a vaccinated melanoma patient" *Proc. Natl. Acad. Sci. USA* 93(13):6280-6285 (Jun. 25, 1996).

Campbell et al., "Essential Role of Interferon-γ and Interleukin-6 Autoimmune Insulin-dependent Diabetes in NOD/Wehi Mice" *J. Clin. Invest.* 87:739 (Feb. 1991).

Carter et al., "Humanization of an Anti-p185$^{HER2}$ Antibody for Human Cancer Therapy" *Proc Natl Acad Sci U S A.* 89(10):4285-4289 (May 1992).

Castano and Eisenbarth, "Type-I Disbetes: A chronic Autoimmune Disease of Human, Mouse, and Rat" *Ann. Rev. Immunol.* 8:647-679 (1990).

Chakrabarti et al., "Control of Islet Intercellular Adhesion Molecule-I Expression by Interferon-α and Hypoxia" *Diabetes* 45:1336-1343 (Oct. 1996).

Chakrabarti et al., "IFN-α Induces Autoimmune T Cells Through the Induction of Intracellular Adhesion Molecule-1 and B7.2" *The Journal of Immunology* 157:522-528 (1996).

Chehadeh et al., "Increased Level of Interferon-α in Blood of Patients with Insulin-Dependent Diabetes Mellitus: Relationship with Coxsackievirus B Infection" *J. of Infectious Diseases* 181:1929-1939 (2000).

Clark, M., "Antibody Humanization: a case of the 'Emperor's new clothes'?" *Immunology Today* 21(8):397-401 (Aug. 2000).

Clothia et al., "Conformations of immunoglobulin hypervariable regions" *Nature* 342:877-883 (Dec. 1989).

Colamonici & Domanski, "Identification of a novel subunit of the type I interferon receptor localized to human chromosome 21" *Journal of Biological Chemistry* 268(15):10895-10899 (1993).

Dall'Acqua, W. et al., "Antibody Engineering" *Current Opinion in Structural Biology* 8:443-450 (1998).

Dansky-Ullmann et al., "Synergistic effects of IL-6 and IFN-γ on carcinembryonic antigen (CEA) and HLA expression by human colorectal carcinoma cells: role of endogenous IFN-β" *Cytokine* 7:118-129 (1995).

Desmyter et al., "Three Camelid VHH Domains in Complex With Porcine Pancreatic α-Amylase" *J Biol Chem.* 277(26):23645-23650 (Jun. 28, 2002).

Dhib-Jalbut et al., "Direct evidence that interferon-β mediates enhances HLA-class I expression in measles virus-infected cells" *J. Immunol.* 151:6248-6252 (1993).

Eaton et al., "Construction and characterization of an active factor VIII variant lacking the central one-third of the molecule" *Biochemistry* 25:8343-8347 (1986).

Edge et al., "Chemical synthesis of a human interferon-$\alpha_2$ gene and its expression in *Escherichia coli*" *Nucleic Acids Research* 11:6419-6435 (1983).

Eigenbrot et al., "X-Ray Structures of Fragments From Binding and Nonbinding Versions of a Humanized Anti-CD18 Antibody: Structural Indications of the Key Role of $V_H$ Residues 59 to 65" *Proteins: Structure, Function, and Genetics* 18:49-62 (1994).

Exley et al., "A comparison of the neutralizing properties of monoclonal and polyclonal antibodies to human interferon alpha" *Journal of General Virology* 65:2277-2280 (1984).

Fabris et al., "Insulin-dependent diabetes mellitus during alpha-interferon therapy for chronic viral hepatitis" *J. of Hepatology* 28:514-517 (1996).

Foote et al., "Antibody Framework Residues Affecting the Conformation of the Hypervariable Loops" *J. Mol. Biol.* 224:487-499 (1992).

Foulis et al., "Immunoreactive $\alpha$-interferon in insulin-secreting $\beta$ cells in type 1 diabetes mellitus" *Lancet* pp. 1423-1427 (Dec. 19, 1987).

Garcia-Porrua et al., "Simultaneous development of SLE-like syndrome and auto-immune thyroids following $\alpha$-interferon treatment" *Letters to Editor* pp. 107-108.

Glennie and Johnson, "Clinical Trials of Antibody Therapy" *Immunology Today* 21(8):403-410 (2000).

Gorman et al., "Transient Production of Proteins Using an Adenovirus Transformed Cell Line" *DNA Prot. Eng. Tech.* 2(1):3-10 (1990).

Gresser, I, "Wherefore interferon?" *J. of Leukocyte Biology* 61:567-574 (1997).

Heim, M. H., "The jak-STAT Pathway: Cytokine Signalling from the Receptor to the Nucleus" *J. of Receptor & Signal Transduction Research* 19(104):75-120 (1999).

Hoogenboom et al., "Natural and designed binding cites made by phage display technology" *Immunology Today* 21(8):371-378 (Aug. 2000).

Hooks et al., "Multiple Interferons in the Circulation of Patients with Systemic Lupus Erythematosus and Vasculitis" *Arthritis and Rheumatism* 25(4):396-400 (Apr. 1982).

Horton et al., "Antitumor Effects of Interferon-to: In Vivo Therapy of Human Tumor Xenografts in Nude Mice" *Cancer Research* 59:4064-4068 (1999).

Horvath et al., "A STAT protein domain that determines DNA sequence recognition suggests a novel DNA-binding domain" *Genes & Development* 9:984-994 (1995).

http://www.researchd.com/cytokines/ifnachrt.htm (On Line Catalog Data Sheet for Anti-Interferon Alpha Antibodies available from Research Diagnostics, Rev. Mar. 8, 2001 (Printed Feb. 10, 2004)).

Huang et al., "Interferon Expression in the Pancreases of Patients with Type I Diabetes" *Diabetes* 44:658-664 (Jun. 1995).

Huang, X. et al., "Islet expression of interferon-$\alpha$ precedes diabetes in both the BB rat and streptozotocin-treated mice" *Immunity* 1:469-478 (1994).

Hudson, P. J., "Recombinant antibody constructs in cancer therapy" *Current Opinion in Immunology* 11:548-557 (1999).

Janeway et al. *Immunobiology*, Garland Science, 6th edition pp. 110-112 (2004).

John et al., "Isolation and Characterization of a New Mutant Human Cell Line Unresponsive to Alpha and Beta Interferons" *Molecular & Cellular Biology* 11(8):4189-4195 (Aug. 1991).

Jones et al., "Endocrine-Mediated Mechanisms of Fatigue During Treatment with Interferon-Alpha." *Seminars in Oncology* (Suppl. 1, Abstract Only) 25(1):54-63 (Feb. 1998).

Jones et al., "Replacing the Complementarity-Determining Regions in a Human Antibody with Those From a Mouse" *Nature* 321(6069):522-525 (May 29, 1986).

Kabat et al., "Sequences of Proteins of Immunological Interest" *U.S. Dept. of Health and Human Services* (Publication No. 91-3242), Fifth edition (1991).

Kanayama et al., "Serum levels of interferon in patients with systemic lupus erythematosus" *Clin. Exp. Immunol.* 70:562-569 (1987).

Kandefer-Szerszen and Lungren, "Three Seprate Epitopes on Human IFN-$\alpha$ Variants Definet by Monoclonal Antibodies and Their Role in the Binding to Receptors" *Archivum Immunoloqiae et Therapae Experimentalis* 40:241-246 (1992).

Kay et al., "The Beta Cell in Autoimmune Diabetes: Many Mechanisms and Pathways of Loss" *TEM* 11(1):11-15 (2000).

King et al., "Characterization and properties of a modified human interferon-alpha containing an additonal 18 amino acids at the N-Terminus" *J. Gen. Virol.* 64(Pt 8):1815-1818 (Aug. 1983).

Kobiler et al., "Production of Monoclonal Antibodies Toward Bovine Interferons-$\alpha$ Suitable for Immunopurification" *J. Interferon Res.* 9(2):189-193 (1989).

Kontsek et al., "Antigenic Link Between human Interferons-$\alpha$ and -$\beta$: The Common Epitope1" *J. of Interferon Research* 10:119-128 (1999).

Kontsek et al., "Mapping of two immunodominant structures of human interferon alpha 2c and their role in binding to cells" *Mol Immunol.* 28(11):1289-1297 (Nov. 1991).

Kontsek, P., et al., "Enhancement of neutralizing efficacy by combining three monoclonal antibodies to human interferon-alpha" *Immunology* 73:8-11 (1991).

Kostrov et al., "[Limited proteolysis of human leukocyte interferon-alpha2 and localization of the antigenic determinant binding the monoclonal antibodies]" *Biokhimiia* (Abstract only) 50(11):1859-1865 (Nov. 1985).

Kudela et al., "Conformational Changes in Ph2-Treated Human Interferon-Alpha 2 Detected with Monoclonal Antibodies" *Hybrodoma* 15(3):185-189 (Nov. 1996).

Kunkel, T., "Rapid and Efficient Site-Specific Mutagenesis Without Phenotypic Selection" *Proc. Natl. Acad. Sci.* 82(2):488-492 (Jan. 1985).

Kurabayashi et al., "Doxorubicin-Induced Id2A Gene Transcription Is Targeted at an Activation Transcription Factor/Cyclic AMP Response Element Mot through Novel Mechanisms Involving Protein Kinases Distinct from Protein Kinase C and Protein Kinase A" *Molecular & Cellular Biology* 14(11):6386-6397 (Nov.

Lacki et al., "Cytokine concentration in serum of Lupus erythematosus patients: the effect on acute phase response" *J. of Medicine* (Nos. 1 & 2) 28:99-107 (1997).

Lau et al., "Interferon regulatory factor subcellular localization is determined by a bipartite nuclear localization signal in the DNA-binding domain and interaction with cytoplasmic retention factors" *Proc. Natl. Acad. Sci. USA* 97(13):7278-7283 (Jun. 2000).

Laurent et al., "Purification of the Major Species of Human Leucocyte Interferon With the Help of a Monoclonal Antibody" *Dev. Biol. Stand*, Switzerland 57:305-310 (1984).

Lefevre et al., "Interferon-delta: The first member of a novel type I interferon family" *Biochimic* 80:779-788 (1998).

Little et al., "Of Mice and Men: Hybridoma and Recombinant Antibodies." *Immunology Today* 21(8):364-370 (Aug. 2000).

Liu, P. T. et al., "High-Yield Expression and Purification of Human Interferon $\alpha$-1 in *Pichia pastoris*" *Protein Exp. Purif.* 22(3):381-387 (Aug. 2001).

Lydon et al., "Immunochemical Mapping of $\alpha$-2 Interferon" *Biochemistry* 24:4131-4141 (1985).

Mannel et al., "A rat monoclonal antibody against mouse $\alpha$ and $\beta$ interferon of all molecular weight species" *Nature* 296:664-665 (Apr. 15, 1982).

Matsumoto et al., "Activation of the Transcription Factor ISGF3 by Interfereon-$\gamma$" *Biol. Chem.* 380:699-703 (Jun. 1998).

McKendry, R. et al., "High-Frequency Mutagenesis of Human Cells and Characterization of a Mutant Unresponsive to both $\alpha$ and $\gamma$ Interferons" *Proc. Natl. Acad. Sci. USA* 88:11455-11459 (1991).

Meager and Berg, "Epitope Localization of a Monoclonal Antibody, LO-22, With Broad Specificity for Interferon-$\alpha$ Subtypes" *J. of Interferon Research* 6:729-736 (1986).

Meager et al., "Development of Interferon-Specific Monoclonal Antibody for In Vitro Interferon Assays" *Dev. Biol. Stand.* 64:237-248 (1986).

Meager, A., "Natural Autoantibodies to Interferons" *J. of Interferon and Cytokine Research* (Sup 1) 17:S51-S53 (1997).

Milstein, C., "With the benefit of hindsight" *Immunology Today* 21(8):359-364 (Aug. 2000).

Morser et al., "Production and screening of cell hybrids producing a monoclonal antibody to human interferon-alpha" *J. Gen. Virol.* 53(Pt 2):257-265 (Apr. 1981).

Noll et al., "Production and characterization of four monoclonal antibodies specific for human interferon-alpha-1 and -alpha-2" *Biomedica Biochimica Acta* 48(1):165-176 (1989).

Noraz, N. et al., "Human Cytomegalovirus-Associated Immunosuppression Is Mediated Through Interferon-α" *Blood* 89:2443-2452 (Apr. 1997).

Novak et al., "Preparation and Characterization of Hybridomas Producing Monoclonal Antibodies Against Human Alpha Interferon" *Acta Virol.* 30(3):228-233 (1986).

Okanoue Takeshi et al., "Side Effects of High-Dose Interferon Therapy for Chronic Hepatitis C." *J. Hepatology* (Abstract Only) 25(3):283-291 (1996).

Osheroff, P. L. et al., "Monoclonal antibodies to a recombinant human leukocyte interferon (rIFN-αB)" *Clinical Immunology and Immunopathology* 30(2):188-196 (Feb. 1984).

Presta et al., "Humanization of an Antibody Directed Against IgE" *J Immunol.* 151(5):2623-2632 (Sep. 1, 1993).

Protzman et al., "Immunoradiometric assay of a recombinant human alpha-2 interferon (SCH 30500)" *J. Clin. Microbiol.* 22(4):596-599 (Oct. 1985).

Prummer, O., et al., "Interferon-α Antidobies in Autoimmune Diseases" *Journal of Interferon Research* 9 (Suppl. 1):S67-S74 (1989).

Rabinovitch, A., "An update on cytokines in the pathogenesis of insulin-dependent diabetes mellitus" *Diabetes-Metabolism Reviews* 14(2):129-151 (Jun. 1998).

Reichert, J., "New biopharmaceuticals in the USA: trends in development and marketing approvals 1995 1999" *TIBTECH* 18:364-369 (Sep. 2000).

Rhodes, C. J. et al., "Effect of human lymphoblastoid interferon on insulin synthesis and secretion in isolated human pancreatic islets" *Diabetologia* 27(6):601-603 (Dec. 1984).

Robak et al., "Association of Interferon y, Tumor Necrosis Factor a and Interleukin 6 Serum Levels with Systemic Lupus Eruthematosus Activity" *Aechiv Immunolooiaw et Therapiaw Experimentalis* 46:375-380 (1998).

Roberts et al., "The Evolution of the Type I Interferons" *J. of Interferon and Cytokine Research* 18:805-806 (1998).

Ronnblom et al., "Case Report, Possible induction of systemic lupus erythematosus by interfereon-α treatment in a patient with a malignant carcinoid tumour" *J. of Internal Medicine* 227:207-210 (1990).

Rudikoff et al., "Single amino acid substitution altering antigen-binding specificity" *Proc. Natl. Acad. Sci. USA* 79:1979-1983 (Mar. 1982).

Sattayasai et al., "Universal Antibodies to Human Interferon-α Subtypes—The Production of Antipeptide Antibodies to Conserved Regions of Interferon-α" *J. of Interferon Research* 11:41-48 (1991).

Schmeisser et al., "Radioiodination of human interferon-alpha2 interferes with binding of C-terminal sepcific antibodies" *J. Immunol. Methods* 238(1-2):81-85 (Apr. 21, 2000).

Secher et al., "A monoclonal antibody for large-scale purification of human leukocyte interferon" *Nature* 285(5765):446-450 (Jun. 12, 1980).

Seifarth et al., "Augmented Immune Response to Islet Cell Anitgens and Development of Diatetes Mellitus Under Treatment with Interferon-Alpha in Chronic Hepatitis C." *Zeitschrift Fuer Gastroenterologie* (Abstract Only) 37(3):235-239 (Mar. 1999).

Shearer et al., "Monoclonal antibodies that distinguish between subspecies of human interferon-α and that detect interferon oligomers" *Journal of Immunology* 133(6):3096-3101 (Dec. 1984).

Shehaden and Lafferty, "The role of T-cells in the development of autoimmune diabetes" *Diabetes Reviews* 1(2):141-151 (1993).

Shiozawa et al., "Interferon-Alpha in ludus Psychosis" *Arthritis and Rheumatism* 35(41):417-422 (Apr. 1992).

Shou-Nee et al., "Serum interferon in systemic lupus erythematosus" *British Journal of Dermatology* 117:155-159 (1987).

Slocombe, P., et al., "High-Level Expression of an Interferon α 2 Gene Cloned in Phage M13mp7 and Subsequent Purification with a Monoclonal Antibody" *Proc. Natl. Acad. Sci. USA* 79:5455-5459 (1982).

Slocombre et al., "High-level expression of an interferon alpha2 cloned in phage M13mp7 and subsequent purification with a monoclonal antibody" *Proc Natl Acad Science USA* 79(18):5455-5459 (Sep. 1982).

Sobel et al., "Alpha Interferon Administration Paradoxically Inhibits the Development of Diabetes in BB Rats" *Life Sciences* 62(15):1293-1302 (1998).

Sobel, D.O. et al., "Alpha-interferon inhibits the development of diabetes in NOD mice" *Diabetes* 47:1867-1872 (Dec. 1998).

Somoza et al., "Pancreas in Recent Onset Insulin-Dependent Mellitus" *The Journal of Immunology* 153(3):1360-1377 (1994).

Staehelin et al., "Purification and characterization of recombinant human leukocyte interferon (IFLrA) with monoclonal antibodies" *Journal of Biological Chemistry* 256:9750-9754 (1981).

Staehelin, et al., "Production of hybridomas secreting monoclonal antibodies to the human leukocyte interferons" *Proc. Natl. Acad. Sci. USA* 78(3):1848-1852 (Mar. 1981).

Stewart et al., "Induction of Type 1 Diabetes by Interferon-A in Transgenic Mice" *Science* 260:1942-1946 (1993).

Subauste, C. S., et al., "Role of CD80 (B7.1) and CD86 (B7.2) in the Immune Response to an Intracellular Pathogen" *J. Immunol.* 160:1831-1840 (1998).

Tanaka-Kataoka et al., "Oral Use of Interferon-α Delays the Onset of Insulin-Dependent Diabetes Mellitus in Nonobese Diabetes Mice" *J. of Interferon and Cytokine Research* 19:877-879 (1999).

Taylor-Papadimitriou, "Epitopes of Human Interferon-α Defined by the Reaction of Monoclonal Antibodies with α Interferons and Interferon Analogues" *J. Immunol.* 139(10):3375-3381 (1987).

Tramontano et al., "Framework residue 71 is a major determinant of the postion and conformation of the second hypervariable region in the $V_H$ domains of immunoglobulins" *J. Mol. Biol.* 215(1):175-182 (Sep. 5, 1990).

Tsukui et al., "A monoclonal antibody with broad reactivity to human interferon-α subtypes useful for purification of leukocyte-derived interferon" *Microbiology & Immunology* 30(11):1129-1139 (1986).

Vaughan et al., "Human Antibodies With Sub-nanomolar Affinities Isolated From a Large Non-immunized Phage Display Library" *Nature Biotechnology* 14:309-314 (Mar. 1996).

Veenstra et al., "IL-12 induces monocyte IL-18 binding protein expression via IFN-γ" *J. Immunol.* 168:2282-2287 (2002).

Viscomi, G. C., et al., "Antigenic Characterization of Recombinant, Lymphoblastoid, and Leukocyte IFN-α by Monoclonal Antibodies" *Journal of Interferon & Cytokine Re* 19(4):319-326 (1999).

Waguri et al., "Occurrence of IDDM during interferon therapy for chronic viral hepatitis" *Diabetes Research and Clinical Practice* 23:33-36 (1994).

Wathelet, M. G. et al., "Virus Infection Induces the Assembly of Coordinately Activated Transcription Factors on the IFN-β Enhancer In Vivo" *Molecular Cell* 1:507-518 (1998).

Werther et al., "Humanization of an Anti-Lymphocyte Function-Associated Antigen (LFA)-1 Monoclonal Antibody and Reengineering of the Humanized Antibody for Binding to Rhesus LFA-1" *J. of Immunology* 157:4986-4995 (1996).

Whittall, J.T.D., et al., "The Reaction of the Anti-Interferon-α Monoclonal Antidoby, NK2, with Different Interferons" *J. Gen. Virol.* 65:629-633 (1984).

Wussow et al., "Presence of interferon and anti-interferon in patients with systemic lupus erythematosus" *Rheumatol. Int.* 8:225-230 (1988).

Xiang, J. et al., "Framework Residues 71 and 93 of the Chimeric B72.3 Antibody are Major Determinants of the Conformation of Heavy-chain Hypervariable Loops" *Journal of Molecular Biology* 253(3):385-390 (Oct. 1995).

Ytterberg, S. R. et al., "Serum interferon levels in patients with systemic lupus erythematosus" *Arthritis and Rheumatism* 25(4):401-406 (Apr. 1982).

Zapata et al., "Engineering Linear F(ab')$_2$ Fragments for Efficient Production in *Escherichia coli* and Enhanced Antiproliferative Activity" *Protein Engineering* 8(10):1057-1062 (Oct. 8, 1995).

Zella, D., et al., "IFN-α2b Reduces IL-2 Production and IL-2 Receptor Function in Primary CD4+ T Cells" *J Immunol* 164:2296-2302 (2000).

Zoon, K. C., et al., "Purification and characterization of multiple components of human lymphoblastoid Interferon-α" *Journal of Biological Chemistry* 267:15210-15216 (1992).

Hanai, N. ((Nov. 1996). "Establishment of Humanized Antibody," *Biotherapy* 10(11):1384-1391. (English Abstract Summary Included.).

Janeway, C.A. et al. (1997). "Structure of the Antibody Molecule and Immunoglobulin Genes," Chapter 3 in *Immunobiology: The Immune System in Health and Disease*, 3$^{rd}$ Ed., Garland Press, New York, New York, pp. 3:7-3:11.

Janeway, C.A. et al. (2005). "Antigen Recognition by B-cell and T-cell Receptors," Chapter 3 in *Immunobiology: The Immune System in Health and Disease*, 6$^{th}$ Ed., Garland Science, New York, New York, p. 110-112, Table of Contents, pp. xiii-xxiii.

Paul, W.E. M. D. ed. (1993). "Immunogenicity and Antigen Structure," Chapter 8 in *Fundamental Immunology*, 3rd Ed., Raven Press, New York, New York, p. 242.

Portolano, S. et al. (Feb. 1, 1993). "Lack of Promiscuity in AutoAntigen-Specific H and L. Chain Combinations as Reveled by Human H and L Chain 'Roulette'," *J. Immunol.* 150(3):880-887.

\* cited by examiner

Figure 5A

Variable Light Domain

```
               1         10         20         30 abcd      40
   murine   DIVLTQSPASLAVSLGQRATISCRASQSVSTSSYSYMHWYQQKPGQPPKVLIS
             **     *   ** * * *   *                        **
   V13      DIQMTQSPSSLSASVGDRVTITCRASQSVSTSSYSYMHWYQQKPGKAPKVLIS
                                      * ***** **                * *
   hukI     DIQMTQSPSSLSASVGDRVTITCRASQSISN----YLAWYQQKPGKAPKLLIY
                                      ----------------

50         60         70         80         90
   murine   YASNLESGVPARFSGSGSGTDFTLNIHPVEEGDTATYFCQHSWGIPRTF
                      *            *  ****** *     *
   V13      YASNLESGVPSRFSGSGSGTDFTLTISSLQPEDFATYYCQHSWGIPRTF
             *  *                                   ***** *
   hukI     AASSLESGVPSRFSGSGSGTDFTLTISSLQPEDFATYYCQQYNSLPWTF
            --------                                ----------

100
   murine   GAGTKLELRRAV
              *    *  ** *
   V13      GQGTKVEIKRTV hukI     GQGTKVEIKRTV
```

Figure 5B

Variable Heavy Domain

```
             1         10        20        30        40
murine   EVQLQQSGPELVKPGASVKISCKTSGYTFTEYIIHWVKQGHGRSLEWIG
           **    **   *   *  ***  *           * ** **    **
V13      EVQLVESGGGLVQPGGSLRLSCATSGYTFTEYIIHWVRQAPGKGLEWVA
                                   *   *  ** ***
huIII    EVQLVESGGGLVQPGGSLRLSCAASGFTFSSYAMSWVRQAPGKGLEWVA
                                 - - - - - - - - - -

50  a    60        70        80  abc     90
murine   SINPDYDITNYNQRFKGKATLTLDKSSRTAYLELRSLTSEDSAVYYCAS
                            ** **     *      *** **   *
V13      SINPDYDITNYNQRFKGRFTISLDKSKRTAYLQMNSLRAEDTAVYYCAS
          * ** *** * ****         * *   *                  *
huIII    VISGDGGSTYYADSVKGRFTISRDNSKNTLYLQMNSLRAEDTAVYYCAR
                  - - - - - - - - - - - - - - - -

100
murine   WISDFFDYWGQGTTLMVSAAS
                      ***   *
V13      WISDFFDYWGQGTLVTVSSAS
         * * * * * *
huIII    GRVGYYDYWGQGTLVTVSSAS
                  - - - - - - - - -
```

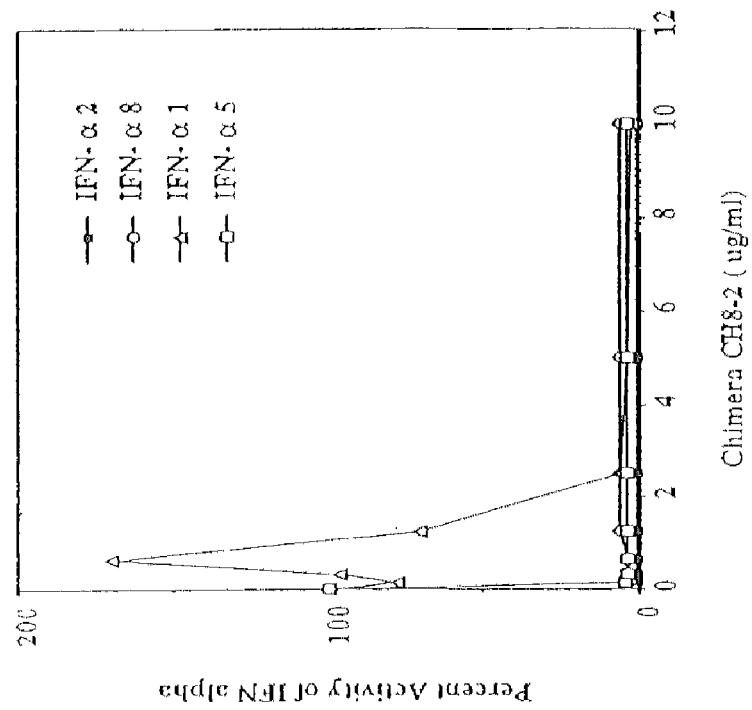
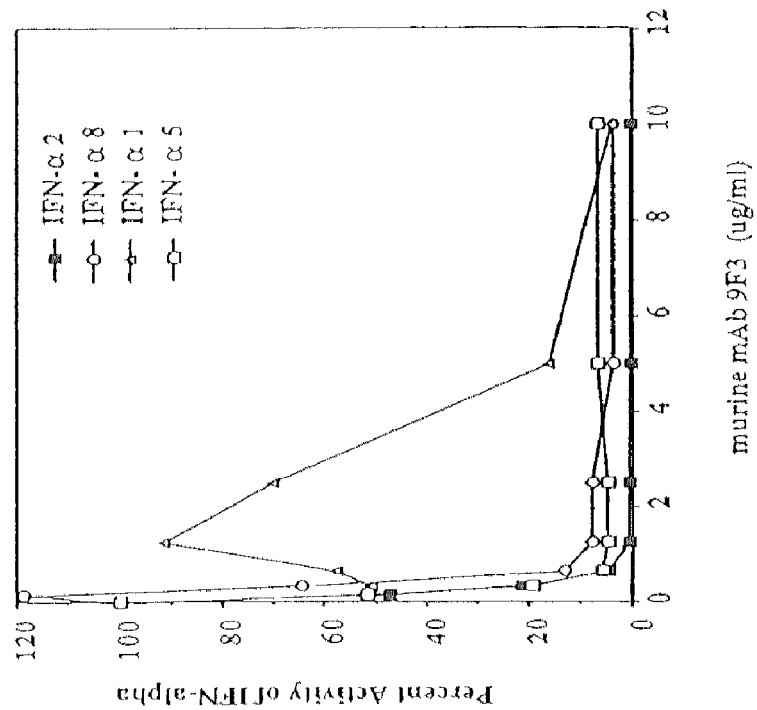
FIGURE 6

ANTI-INTERFERON-α ANTIBODIES

The present application is a Divisional of U.S. patent application Ser. No. 11/423,588 filed on Jun. 12, 2006, now U.S. Pat. No. 7,910,707, which is a continuation of U.S. application Ser. No. 10/044,896, filed on Jan. 9, 2002, now issued as U.S. Pat. No. 7,087,726, which claims priority under 35 U.S.C. §119(e) to Provisional Application No. 60/270,775, filed on Feb. 22, 2001, all of which are hereby incorporated in their entirety by reference.

BACKGROUND OF THE INVENTION

1. Field of the Invention

The present invention relates generally to the generation and characterization of neutralizing anti-IFN-α monoclonal antibodies with broad reactivity against various IFN-α subtypes. The invention further relates to the use of such anti-IFN-α antibodies in the diagnosis and treatment of disorders associated with increased expression of IFN-α, in particular, autoimmune disorders such as insulin-dependent diabetes mellitus (IDDM) and systemic lupus erythematosus (SLE).

2. Description of the Related Art

Interferon-α (IFN-α)

Although interferons were initially discovered for their anti-viral activities, subsequent research has unraveled a plethora of regulatory activities associated with these powerful cytokines. Type I interferons form an ancient family of cytokines that includes IFN-α, IFN-β, IFN-δ, IFN-ω and IFN-τ (Roberts et al., *J. Interferon Cytokine Res.* 18: 805-816 [1998]). They are coded by intronless genes and are widely distributed amongst vertebrates. Whereas IFN-β is coded by a single gene in primates and rodents, more than 10 and 15 different subtypes of IFN-α have been found in mice and man respectively. Other interferons of type I are more restricted, e.g. IFN-δ in the pig, IFN-τ in cattle and sheep, and IFN-ω in cattle and humans. Thus, human type I interferons comprise multiple members of the IFN-α family, and single members of the IFN-β and IFN-ω families. All type I IFNs appear to bind to a single receptor that is comprised of at least two membrane spanning proteins. Type II interferons on the other hand are represented by a single member, IFN-γ, and bind to a distinct receptor.

Although all type I IFNs, including IFN-α, exhibit anti-viral and anti-proliferative activities and thereby help to control viral infections and tumors (Lefevre et al., *Biochimie* 80: 779-788 [1998]; Horton et al., *Cancer Res.* 59: 4064-4068 [1999]; Alexenko et al., *J. Interferon Cytokine Res.* 17: 769-779 [1997]; Gresser, *J. Leukoc. Biol.* 61: 567-574 [1997]), there are also several autoimmune diseases that are associated with increased expression of IFNα, most notably insulin-dependent diabetes mellitus (IDDM) and systemic lupus erythematosus (SLE).

Type I diabetes, also known as autoimmune diabetes or insulin-dependent diabetes mellitus (IDDM), is an autoimmune disease characterized by the selective destruction of pancreatic β cells by autoreactive T lymphocytes (Bach, *Endocr. Rev.* 15: 516-542 [1994]; Castano and Eisenbarth, *Annu. Rev. Immunol.* 8: 647-679 [1990]; Shehadeh and Lafferty, *Diabetes Rev.* 1: 141-151 [1993]). The pathology of IDDM is very complex involving an interaction between an epigenetic event (possibly a viral infection), the pancreatic β cells and the immune system in a genetically susceptible host. A number of cytokines, including IFN-α and IFN-γ, have been implicated in the pathogenesis of IDDM in humans and in animal models of the disease (Campbell et al., *J. Clin. Invest.* 87: 739-742 [1991]; Huang et al., *Diabetes* 44: 658-664 [1995]; Rhodes and Taylor, *Diabetologia* 27: 601-603 [1984]). For example, pancreatic Ifn-α mRNA expression and the presence of immunoreactive IFN-α in β cells of patients with IDDM have been reported (Foulis et al., *Lancet* 2: 1423-1427 [1987]; Huang et al., [1995] supra; Somoza et al., *J. Immunol.* 153: 1360-1377 [1994]). IFN-α expression has been associated with hyperexpression of major histocompatibility complex (MHC) class $I_A$ antigens in human islets (Foulis et al., [1987] supra; Somoza et al., [1994] supra). In two rodent models of autoimmune diabetes, the diabetes-prone DP-BB rat and streptozotocin-treated mice, Ifn-α mRNA expression in islets precedes insulitis and diabetes (Huang et al., *Immunity* 1: 469-478 [1994]). Furthermore, transgenic mice harboring a hybrid human insulin promoter-Ifn-α construct develop hypoinsulinemic diabetes accompanied by insulitis (Stewart et al., *Science* 260: 1942-1946 [1993]).

It appears that local expression of IFN-α by pancreatic islet cells in response to potential diabetogenic stimuli such as viruses may trigger the insulitic process. Consistent with its role as an initiating agent, IFN-α has been shown to induce intercellular adhesion molecule-1 (ICAM-1) and HLA class $I_A$ on endothelial cells from human islets, which may contribute to leukocyte infiltration during insulitis (Chakrabarti et al., *J. Immunol.* 157: 522-528 [1996]). Furthermore, IFN-α facilitates T cell stimulation by the induction of the co-stimulatory molecules ICAM-1 and B7.2 on antigen-presenting cells in islets (Chakrabarti et al., *Diabetes* 45: 1336-1343 [1996]). These studies collectively indicate that early IFN-α expression by β cells may be a critical event in the initiation of autoimmune diabetes. Although there are a number of reports implicating IFN-γ in the development of IDDM in rodent models, there is a poor correlation between the expression of this cytokine and human IDDM. Thus, cells expressing IFN-γ can be found in the islets of a subset of human patients selected for significant lymphocytic infiltration into the islets. In a group of patients that were not selected by this criterion there was no obvious association between IFN-γ expression and human IDDM.

Based on the increased level of IFN-α expression in patients with systemic lupus erythematosus (SLE), IFN-α has also been implicated in the pathogenesis of SLE (Ytterberg and Schnitzer, *Arthritis Rheum.* 25: 401-406 [1982]; Shi et al., *Br. J. Dermatol.* 117: 155-159 [1987]). It is interesting to note that IFN-α is currently used for the treatment of cancer as well as viral infection such as chronic hepatitis due to hepatitis B or hepatitis C virus infection. Consistent with the observations of increased levels of IFN-α triggering autoimmunity, significant increase in the appearance of autoimmune disorders such as IDDM, SLE and autoimmune thyroiditis has been reported in the patients undergoing IFN-α therapy. For example, prolonged use of IFN-α as an anti-viral therapy has been shown to induce IDDM (Waguri et al., *Diabetes Res. Clin. Pract.* 23: 33-36 [1994]; Fabris et al., *J. Hepatol.* 28: 514-517 [1998]) or SLE (Garcia-Porrua et al., *Clin. Exp. Rheumatol.* 16: 107-108 [1998]). The treatment of coxsackievirus B (CBV) infection with IFN-α therapy is also associated with the induction of IDDM (Chehadeh et al., *J. Infect. Dis.* 181: 1929-1939 [2000]). Similarly, there are multiple case reports documenting IDDM or SLE in IFN-α treated cancer patients (Ronnblom et al., *J. Intern. Med.* 227: 207-210 [1990]).

Antibody Therapy

The use of monoclonal antibodies as therapeutics has gained increased acceptance with several monoclonal antibodies (mAbs) either approved for human use or in late stage clinical trials. The first mAb approved by the US Food and Drug Administration (FDA) for the treatment of allograft rejection was anti-CD3 (OKT3) in 1986. Since then the pace of progress in the field of mAbs has been considerably accelerated, particularly from 1994 onwards which led to approval of additional seven mAbs for human treatment. These include ReoPro® for the management of complications of coronary angioplasty in 1994, Zenapax® (anti-CD25) for the prevention of allograft rejection in 1997, Rituxan® (anti-CD20) for the treatment of B cell non-Hodgkin's lymphoma in 1997, Infliximab® (anti-TNF-α) initially for the treatment of Crohn's disease in 1998 and subsequently for the treatment of rheumatoid arthritis in 1999, Simulect® (anti-CD25) for the prevention of allograft rejection in 1998, Synagis® (anti-F protein of respiratory syncitial virus) for the treatment of respiratory infections in 1998, and Herceptin® (anti-HER2/neu) for the treatment of HER2 overexpressing metastatic breast tumors in 1998 (Glennie and Johnson, *Immunol. Today* 21: 403-410 [2000]).

Anti-IFN-α Antibodies

Disease states that are amenable to intervention with mAbs include all those in which there is a pathological level of a target antigen. For example, an antibody that neutralizes IFN-α present in the sera of patients with SLE, and expressed by the pancreatic islets in IDDM, is a potential candidate for therapeutic intervention in these diseases. It could also be used for therapeutic intervention in other autoimmune diseases with underlying increase in and causative role of IFN-α expression. In both human IDDM (Foulis, et al., *Lancet* 2: 1423-1427 [1987]; Huang, et al., *Diabetes* 44: 658-664 [1995]; Somoza, et al., *J. Immunol.* 153: 1360-1377 [1994]) and human SLE (Hooks, et al., *Arthritis & Rheumatism* 25: 396-400 [1982]; Kim, et al., *Clin. Exp. Immunol.* 70: 562-569 [1987]; Lacki, et al., *J. Med.* 28: 99-107 [1997]; Robak, et al., *Archivum Immunologiae et Therapiae Experimentalis* 46: 375-380 [1998]; Shiozawa, et al., *Arthritis & Rheumatism* 35: 417-422 [1992]; von Wussow, et al., *Rheumatology International* 8: 225-230 [1988]) there appears to be correlation between disease and IFN-α but not with either IFN-β or IFN-γ. Thus, anti-interferon mAb intervention in IDDM or SLE would require specific neutralization of most, if not all, of the IFN-α subtypes, without any significant neutralization of IFN-β or IFN-γ. Leaving the activity of these last two interferons intact may also have an advantage in allowing the retention of significant anti-viral activity.

While a few mAbs that show reactivity with a range of recombinant human IFN-α subtypes have been described, these were found to neutralize only a limited subset of the recombinant MN-α subtypes analyzed or were not capable of neutralizing the mixture of IFN-α subtypes that are produced by stimulated peripheral blood leukocytes (Tsukui et al., *Microbiol. Immunol.* 30: 1129-1139 [1986]; Berg, *J. Interferon Res.* 4: 481-491 [1984]; Meager and Berg, *J. Interferon Res.* 6: 729-736 [1986]; U.S. Pat. No. 4,902,618; and EP publication No. 0,139,676 B1).

Accordingly, there is a great need for anti-IFN-α antibodies that not only bind to most, preferably all, subtypes of IFN-α but also neutralize such subtypes while do not interfere with the biological function of other interferons.

SUMMARY OF THE INVENTION

The present invention is based on the development of a monoclonal antibody that was experimentally found to neutralize all seven of different recombinant human IFN-α subtypes tested and two independent pools of natural human IFN-α subtypes.

In one aspect, the invention provides an anti-human IFN-α monoclonal antibody which binds to and neutralizes a biological activity of at least human IFN-α subtypes IFN-α1, IFN-α2, IFN-α4, IFN-α5, IFN-α8, IFN-α10, and IFN-α21. In a further aspect, the invention provides an anti-human IFN-α monoclonal antibody which binds to and neutralizes a biological activity of all human IFN-α subtypes. The antibody of the invention can significantly reduce or eliminate a biological activity of the human IFN-α in question. In one embodiment, the antibody of the invention is capable of neutralizing at least 60%, or at least 70%, preferably at least 75%, more preferably at least 80%, even more preferably at least 85%, still more preferably at least 90%, still more preferably at least 95%, most preferably at least 99% of a biological activity of the subject human IFN-α. In another embodiment, the human IFN-α biological activity-neutralizing monoclonal antibody does not neutralize the corresponding biological activity of human IFN-β.

The biological activity of the subject human IFN-α's may be IFNAR2-binding activity. In a particular embodiment, the invention provides an anti-human IFN-α monoclonal antibody is capable of binding to and blocking at least 60%, or at least 70%, preferably at least 75%, more preferably at least 80%, even more preferably at least 85%, still more preferably at least 90%, still more preferably at least 95%, most preferably at least 99% of the IFNAR2-binding activity of all, or substantially all human IFN-α subtypes. In another embodiment, the invention provides an anti-human IFN-α monoclonal antibody that is capable of binding to and blocking at least 60%, or at least 70%, preferably at least 75%, more preferably at least 80%, even more preferably at least 85%, still more preferably at least 90%, still more preferably at least 95%, most preferably at least 99% of the IFNAR2-binding activity of each of human IFN-α subtypes 1, 2, 4, 5, 8, 10 and 21. In another embodiment, the anti-human IFN-α monoclonal antibody does not cross-react with human IFN-β.

The biological activity of the subject human IFN-α's may be an antiviral activity. In one embodiment, the anti-human IFN-α monoclonal antibody is capable of binding to and neutralizing the antiviral activity of all, or substantially all human IFN-α subtypes. In another embodiment, the anti-human IFN-α monoclonal antibody is capable of binding to and neutralizing the antiviral activity of each of human IFN-α subtypes 1, 2, 4, 5, 8, 10 and 21. In a particular embodiment, the invention provides an anti-human IFN-α monoclonal antibody that is capable of binding to and neutralizing at least 60%, or at least 70%, preferably at least 75%, more preferably at least 80%, even more preferably at least 85%, still more preferably at least 90%, still more preferably at least 95%, most preferably at least 99% of the antiviral activity of all, or substantially all human IFN-α subtypes. In yet another embodiment, the invention provides an anti-human IFN-α monoclonal antibody which binds to and neutralizes at least 60%, or at least 70%, or at least 75%, or at least 80%, or at least 85%, or at least 90%, or at least 95%, or at least 99% of the antiviral activity of each of human IFN-α subtypes 1, 2, 4, 5, 8, 10 and 21. In still another embodiment, the human IFN-α antiviral activity-neutralizing monoclonal antibody does not neutralize the antiviral activity of human IFN-β.

The antibody may be a murine, humanized or human antibody. The antibody may be the murine anti-human IFN-α monoclonal antibody 9F3 or a humanized version of it such as version 13 (V13) or chimeric form thereof. The scope of the invention also covers an antibody that binds essentially the same IFN-α epitope as murine anti-human IFN-α monoclonal antibody 9F3 or a humanized or chimeric form thereof. For example, a reference antibody for this purpose is an anti-IFN-α antibody produced by the murine hybridoma cell line 9F3.18.5 deposited with ATCC on Jan. 18, 2001 and having accession No. PTA-2917. In another embodiment, the invention provides a murine or murine/human chimeric anti-human IFN-α monoclonal antibody comprising the murine light chain variable domain amino acid sequence shown in FIG. 5A (SEQ ID NO:1) and/or the murine heavy chain variable domain amino acid sequence shown in FIG. 5B (SEQ ID NO:2). In yet another embodiment, the invention provides a humanized anti-human IFN-α monoclonal antibody comprising the humanized light chain variable domain amino acid sequence shown in FIG. 5A (SEQ ID NO:3) and/or the humanized heavy chain variable domain amino acid sequence shown in FIG. 5B (SEQ ID NO:5).

Additionally provided is an anti-human IFN-α monoclonal antibody that binds essentially the same epitopes on human IFN-α subtypes 1, 2, 4, 5, 8, 10 and 21 that are bound by murine anti-human IFN-α monoclonal antibody 9F3 or a humanized or chimeric form thereof. Further provided herein is an anti-human IFN-α monoclonal antibody that competes with murine anti-human IFN-α monoclonal antibody 9F3 for binding to each of human IFN-α subtypes 1, 2, 4, 5, 8, 10 and 21.

Also provided is an isolated nucleic acid molecule encoding any of the antibodies described herein, a vector comprising the isolated nucleic acid molecule, a host cell transformed with the nucleic acid molecule, and a method of producing the antibody comprising culturing the host cell under conditions wherein the nucleic acid molecule is expressed to produce the antibody and optionally recovering the antibody from the host cell. The antibody may be of the IgG class and isotypes such as $IgG_1$, $IgG_2$, $IgG_3$, or $IgG_4$. The scope of the invention also covers antibody fragments such as Fv, scFv, Fab, $F(ab')_2$, and Fab' fragments.

In another aspect, the present invention provides an anti-human IFN-α monoclonal antibody light chain or a fragment thereof, comprising the following CDR's (as defined by Kabat, et al., *Sequences of Proteins of Immunological Interest*, Fifth Edition, NIH Publication 91-3242, Bethesda Md. [1991], vols. 1-3): (a) L1 of the formula RASQSVSTSSYSYMH (SEQ ID NO: 7); (b) L2 of the formula YASNLES (SEQ ID NO: 8); and (c) L3 of the formula QHSWGIPRTF (SEQ ID NO: 9). The scope of the invention also covers the light chain variable domain of such anti-human IFN-α monoclonal antibody light chain fragment. The scope of the invention further includes an anti-human IFN-α monoclonal antibody light chain polypeptide comprising the mouse/human chimeric light chain variable domain amino acid sequence, or the entire chimeric light chain polypeptide amino acid sequence, encoded by the XAIFN-ChLpDR1 vector deposited with the ATCC on Jan. 9, 2001 and having accession No. PTA-2880. The scope of the invention additionally includes an anti-human IFN-α monoclonal antibody light chain polypeptide comprising the humanized light chain variable domain amino acid sequence, or the entire humanized light chain polypeptide amino acid sequence, encoded by the VLV30-IgG vector deposited with the ATCC on Jan. 9, 2001 and having accession No. PTA-2882.

In yet another aspect, the invention provides an anti-human IFN-α monoclonal antibody heavy chain or a fragment thereof, comprising the following CDR's: (a) H1 of the formula GYTFTEYIIH (SEQ ID NO: 10); (b) H2 of the formula SINPDYDITNYNQRFKG (SEQ ID NO: 11); and (c) H3 of the formula WISDFFDY (SEQ ID NO: 12). The scope of the invention also covers the heavy chain variable domain of such anti-human IFN-α monoclonal antibody heavy chain fragment. The scope of the invention further includes an anti-human IFN-α monoclonal antibody heavy chain polypeptide comprising the mouse/human chimeric heavy chain variable domain amino acid sequence, or the entire chimeric heavy chain polypeptide amino acid sequence, encoded by the XAIFN-ChHpDR2 vector deposited with the ATCC on Jan. 9, 2001 and having accession No. PTA-2883. Additionally included is an anti-human IFN-α monoclonal antibody heavy chain polypeptide comprising the humanized heavy chain variable domain amino acid sequence, or the entire humanized heavy chain polypeptide amino acid sequence, encoded by the vector VHV30-IgG2 deposited with the ATCC on Jan. 9, 2001 and having accession No. PTA-2881.

In a further aspect, the invention provides an anti-human IFN-α monoclonal antibody comprising (A) at least one light chain or a fragment thereof, comprising the following CDR's: (a) L1 of the formula RASQSVSTSSYSYMH (SEQ ID NO: 7); (b) L2 of the formula YASNLES (SEQ ID NO: 8); and (c) L3 of the formula QHSWGIPRTF (SEQ ID NO: 9); and (B) at least one heavy chain or a fragment thereof, comprising the following CDR's: (a) H1 of the formula GYTFTEYIIH (SEQ ID NO: 10); (b) H2 of the formula SINPDYDITNYNQRFKG (SEQ ID NO: 11); and (c) H3 of the formula WISDFFDY (SEQ ID NO: 12). The antibody may be a homo-tetrameric structure composed of two disulfide-bonded antibody heavy chain-light chain pairs. The scope of the invention specifically includes a linear antibody, a murine antibody, a chimeric antibody, a humanized antibody, or a human antibody. Further provided is a chimeric antibody comprising (1) the mouse/human chimeric light chain variable domain amino acid sequence, or the entire chimeric light chain polypeptide amino acid sequence, encoded by the XAIFN-ChLpDR1 vector deposited with the ATCC on Jan. 9, 2001 and having accession No. PTA-2880; and (2) the mouse/human chimeric heavy chain variable domain amino acid sequence, or the entire chimeric heavy chain polypeptide amino acid sequence, encoded by the XAIFN-ChHpDR2 vector deposited with the ATCC on Jan. 9, 2001 and having accession No. PTA-2883. Additionally provided herein is a humanized antibody comprising (1) the humanized light chain variable domain amino acid sequence, or the entire humanized light chain polypeptide amino acid sequence, encoded by the VLV30-IgG vector deposited with the ATCC on Jan. 9, 2001 and having accession No. PTA-2882; and (2) the humanized heavy chain variable domain amino acid sequence, or the entire humanized heavy chain polypeptide amino acid sequence, encoded by the vector VHV30-IgG2 deposited with the ATCC on Jan. 9, 2001 and having accession No. PTA-2881.

In yet another aspect, the invention provides a pharmaceutical composition comprising an effective amount of the antibody of the invention in admixture with a pharmaceutically acceptable carrier.

In a different aspect, the invention provides a method for diagnosing a condition associated with the expression of IFN-α in a cell, comprising contacting the cell with an anti-IFN-α antibody, and detecting the presence of IFN-α.

In yet another aspect, the invention provides a method for the treatment of a disease or condition associated with the expression of IFN-α in a patient, comprising administering to the patient an effective amount of an anti-IFN-α antibody. The patient is a mammalian patient, preferably a human patient. The disease is an autoimmune disease, such as insulin-dependent diabetes mellitus (IDDM); systemic lupus erythematosus (SLE); or autoimmune thyroiditis.

BRIEF DESCRIPTION OF THE DRAWINGS

In FIG. 3A, 20,000 IU/ml (filled bars) or 5,000 IU/ml (open bars) of leukocyte interferon (Sigma Product No. I-2396) were incubated with blank control (buffer only) (denoted as "−"), 10 μg/ml control mouse IgG (denoted as "mIgG"), or 10 μg/ml mAb 9F3 (denoted as "9F3"). Dilutions were assayed and the amount of remaining activity shown. The results shown are means of duplicate determinations. In FIG. 3B, lymphoblastoid interferon (NIH reference Ga23-901-532) was assayed at 10 (filled columns) or 3 (open columns) IU/ml in the presence or absence of the indicated concentrations of mAb 9F3. A higher cytopathic effect is indicative of a decrease in interferon activity. The results shown are the means of duplicate determinations.

FIG. 5A shows the alignment of light chain variable domain amino acid sequences of murine 9F3 (murine, SEQ ID NO: 1), humanized 9F3 version 13 (V13, SEQ ID NO: 3), and the consensus human variable domain light κ subgroup I (huκI, SEQ ID NO: 4). The CDRs (L1, SEQ ID NO: 7; L2, SEQ ID NO: 8; and L3, SEQ ID NO: 9) are highlighted by underlining. The residue numbering is according to Kabat et al., (1991) supra. The differences between the murine 9F3 and V13 sequences and the differences between 9F3 and hind sequences are indicated by asterisks.

FIG. 5B shows the alignment of heavy chain variable domain amino acid sequences of murine 9F3 (murine, SEQ ID NO: 2), humanized 9F3 version 13 (V13, SEQ ID NO: 5), and the consensus human variable domain heavy subgroup III (huIII, SEQ ID NO: 6). The CDRs (H1, SEQ ID NO: 10; H2, SEQ ID NO: 11; and H3, SEQ ID NO: 12) are highlighted by underlining. The residue numbering is according to Kabat et al. (1991) supra. The differences between the murine 9F3 and V13 sequences and the differences between 9F3 and huII sequences are indicated by asterisks.

FIG. 6 shows neutralization activity of the starting mAb 9F3 (left panel) and the chimeric protein CH8-2 (right panel) toward the viral growth inhibition exhibited by recombinant IFN-α subtypes in A549 cells challenged with encephalomyocarditis (EMC) virus.

DETAILED DESCRIPTION OF THE PREFERRED EMBODIMENT

A. Definitions

Unless defined otherwise, technical and scientific terms used herein have the same meaning as commonly understood by one of ordinary skill in the art to which this invention belongs. See, e.g. Singleton et al., *Dictionary of Microbiology and Molecular Biology* 2nd ed., J. Wiley & Sons (New York, N.Y. 1994); Sambrook et al., *Molecular Cloning, A Laboratory Manual*, Cold Springs Harbor Press (Cold Springs Harbor, N.Y. 1989). For purposes of the present invention, the following terms are defined below.

As used herein, the term "type I interferon" is defined to include all subtypes of native sequence type I interferons of any mammalian species, including interferon-α, interferon-β, interferon-δ, interferon-ω and interferon-τ. Similarly, the term "human type I interferon" is defined to include all subtypes of native sequence type I human interferons, including human interferon-α, interferon-β and interferon-ω classes and which bind to a common cellular receptor.

Unless otherwise expressly provided, the terms "interferon-α," "IFN-α," and "human interferon-α", "human IFN-α" and "hIFN-α" are used herein to refer to all species of native sequence human alpha interferons, including all subtypes of native sequence human interferons-α. Natural (native sequence) human interferon-α comprises 23 or more closely related proteins encoded by distinct genes with a high degree of structural homology (Weissmann and Weber, *Prog. Nucl. Acid. Res. Mol. Biol.*, 33: 251 [1986]; *J. Interferon Res.*, 13: 443-444 [1993]; Roberts et al., *J. Interferon Cytokine Res.* 18: 805-816 [1998]). The human IFN-α locus comprises two subfamilies. The first subfamily consists of at least 14 functional, non-allelic genes, including genes encoding IFN-αA (IFN-α2), IFN-αB (IFN-α8), IFN-αC (IFN-α10), IFN-αD (IFN-α1), IFN-αE (IFN-α22), IFN-αF (IFN-α21), IFN-αG (IFN-α5), and IFN-αH (IFN-α14), and pseudogenes having at least 80% homology. The second subfamily, $α_H$ or ω, contains at least 5 pseudogenes and one functional gene (denoted herein as "IFN-$α_H$1" or "IFN-ω") which exhibits 70% homology with the IFN-α genes (Weissmann and Weber [1986] supra).

As used herein, the terms "first human interferon-α (hIFN-α) receptor", "IFN-αR", "hIFNAR1", "IFNAR1", and "Uze chain" are defined as the 557 amino acid receptor protein cloned by Uze et al., *Cell*, 60: 225-234 (1990), including an extracellular domain of 409 residues, a transmembrane domain of 21 residues, and an intracellular domain of 100 residues, as shown in FIG. 5 on page 229 of Uze et al. Also encompassed by the foregoing terms are fragments of IFNAR1 that contain the extracellular domain (ECD) (or fragments of the ECD) of IFNAR1.

Figure 1:
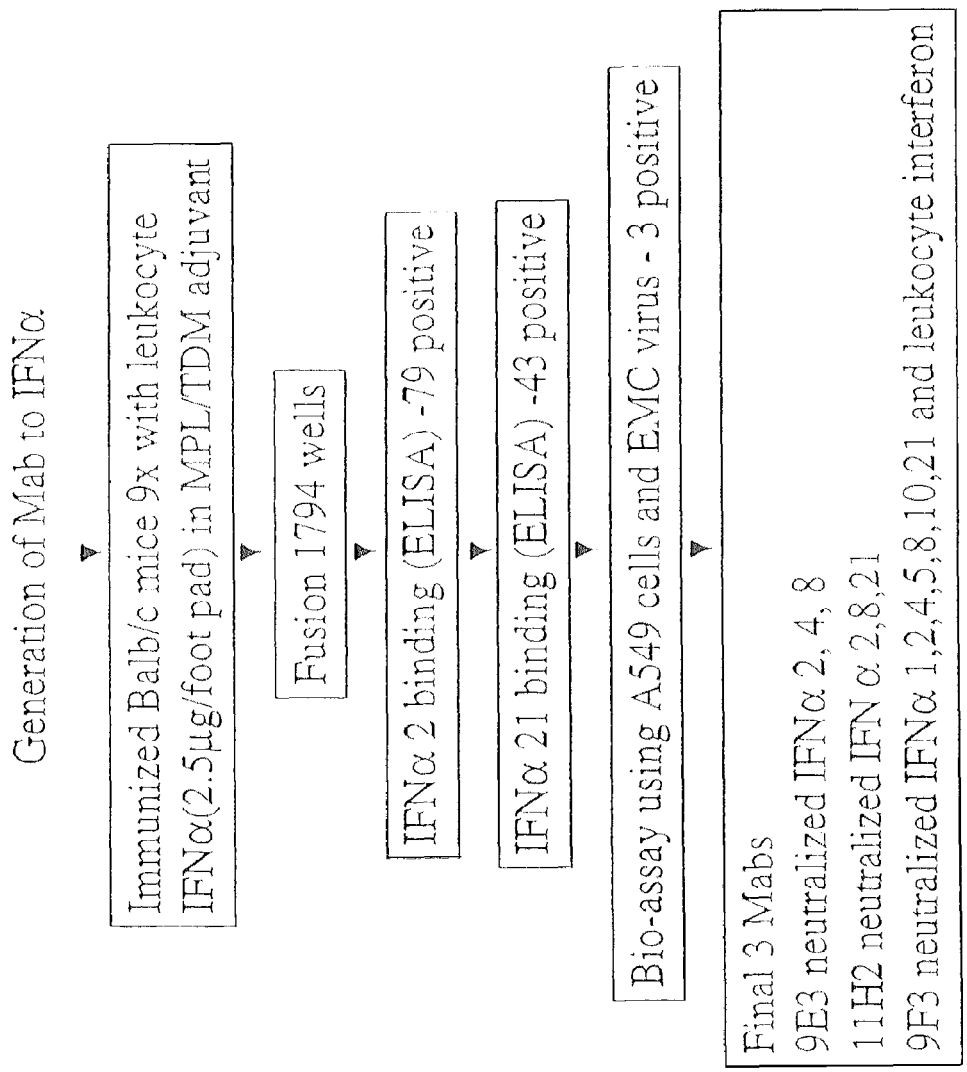
FIG. 1 shows a schematic diagram of the strategy used for the development of the anti-human IFN-α monoclonal antibodies.

As used herein, the terms "second human interferon-α (hIFN-α) receptor", "IFN-αβR", "hIFNAR2", "IFNAR2", and "Novick chain" are defined as the 515 amino acid receptor protein cloned by Domanski et al., *J. Biol. Chem.*, 37: 21606-21611 (1995), including an extracellular domain of 217 residues, a transmembrane domain of 21 residues, and an intracellular domain of 250 residues, as shown in FIG. 1 on page 21608 of Domanski et al. Also encompassed by the foregoing terms are fragments of IFNAR2 that contain the extracellular domain (ECD) (or fragments of the ECD) of IFNAR2, and soluble forms of IFNAR2, such as IFNAR2 ECD fused to an immunoglobulin sequence, e.g. IFNAR2 ECD-IgG Fc as described below.

The term "native sequence" in connection with type I interferon, IFN-α or any other polypeptide refers to a polypeptide that has the same amino acid sequence as a corresponding polypeptide derived from nature, regardless of its mode of preparation. Such native sequence polypeptide can be isolated from nature or can be produced by recombinant and/or synthetic means or any combinations thereof. The term "native sequence" specifically encompasses naturally-occurring truncated or secreted forms (e.g., an extracellular domain sequence), naturally-occurring variant forms (e.g., alternatively spliced forms) and naturally-occurring allelic variants of the full length polypeptides.

"Polymerase chain reaction" or "PCR" refers to a procedure or technique in which minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.* 51:263 (1987); Erlich, ed., *PCR Technology* (Stockton Press, NY, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Chothia et al., *J. Mol. Biol.* 186:651 [1985]; Novotny and Haber, *Proc. Natl. Acad. Sci. U.S.A.* 82:4592 [1985]; Chothia et al., *Nature* 342: 877-883 [1989]).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al. (1991) supra). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called κ and λ, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$, IgA$_1$, and IgA$_2$. The heavy-chain constant domains that correspond to the different classes of immunoglobulins are called α, δ, ε, γ, and μ respectively. The subunit structures and three-dimensional configurations of different classes of immunoglobulins are well known.

The term "antibody" includes all classes and subclasses of intact immunoglobulins. The term "antibody" also covers antibody fragments. The term "antibody" specifically covers monoclonal antibodies, including antibody fragment clones.

"Antibody fragments" comprise a portion of an intact antibody that contains the antigen binding or variable region of the intact antibody. Examples of antibody fragments include Fab, Fab', F(ab')$_2$, and Fv fragments; diabodies; single-chain antibody molecules, including single-chain Fv (scFv) molecules; and multispecific antibodies formed from antibody fragments.

The term "monoclonal antibody" as used herein refers to an antibody (or antibody fragment) obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, and are not contaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 (1975), or may be made by recombinant DNA methods (see, e.g., U.S. Pat. No. 4,816,567). The "monoclonal antibodies" also include clones of antigen-recognition and binding-site containing antibody fragments (Fv clones) isolated from phage antibody libraries using the techniques described in Clackson et al., Nature, 352:624-628 (1991) and Marks et al., J. Mol. Biol., 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 to Cabilly et al.; Morrison et al., Proc. Natl. Acad. Sci. USA, 81:6851-6855 [1984]).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from part or all of a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321:522-525 (1986); Reichmann et al., Nature, 332: 323-329 (1988); Presta, Curr. Op. Struct. Biol., 2:593-596 (1992); and Clark, Immunol. Today 21: 397-402 (2000). The humanized antibody includes a Primatized™ antibody wherein the antigen-binding region of the antibody is derived from an antibody produced by immunizing macaque monkeys with the antigen of interest.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains, which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994), Dall'Acqua and Carter, Curr. Opin. Struct. Biol. 8: 443-450 (1998), and Hudson, Curr. Opin. Immunol. 11: 548-557 (1999).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

By "neutralizing antibody" is meant an antibody molecule which is able to eliminate or significantly reduce an effector function of a target antigen to which it binds. Accordingly, a "neutralizing" anti-IFN-α antibody is capable of eliminating or significantly reducing an effector function, such as receptor binding and/or elicitation of a cellular response, of IFN-α.

For the purpose of the present invention, the ability of an anti-IFN-α antibody to neutralize the receptor activation activity of IFN-α can be monitored, for example, in a Kinase Receptor Activation (KIRA) Assay as described in WO 95/14930, published Jun. 1, 1995, by measuring the ability of a candidate antibody to reduce tyrosine phosphorylation (resulting from ligand binding) of the IFNAR1/R2 receptor complex.

For the purpose of the present invention, the ability of the anti-IFN-α antibodies to neutralize the elicitation of a cellular response by IFN-α is preferably tested by monitoring the neutralization of the antiviral activity of IFN-α, as described by Kawade, J. Interferon Res. 1:61-70 (1980), or Kawade and Watanabe, J. Interferon Res. 4:571-584 (1984), or Yousefi, et al., Am. J. Clin. Pathol. 83: 735-740 (1985), or by testing the ability of an anti-IFN-α antibody to neutralize the ability of IFN-α to activate the binding of the signaling molecule, interferon-stimulated factor 3 (ISGF3), to an oligonucleotide derived from the interferon-stimulated response element (ISRE), in an electrophoretic mobility shift assay, as described by Kurabayashi et al., *Mol. Cell Biol.,* 15: 6386 (1995).

"Significant" reduction means at least about 60%, or at least about 70%, preferably at least about 75%, more preferably at least about 80%, even more preferably at least about 85%, still more preferably at least about 90%, still more preferably at least about 95%, most preferably at least about 99% reduction of an effector function of the target antigen (e.g. IFN-α), such as receptor (e.g. IFNAR2) binding and/or elicitation of a cellular response. Preferably, the "neutralizing" antibodies as defined herein will be capable of neutralizing at least about 60%, or at least about 70%, preferably at least about 75%, more preferably at least about 80%, even more preferably at least about 85%, still more preferably at least about 90%, still more preferably at least about 95%, most preferably at least about 99% of the anti-viral activity of IFN-α, as determined by the anti-viral assay of Kawade (1980), supra, or Yousefi (1985), supra. In another preferred embodiment, the "neutralizing" antibodies herein will be capable of reducing tyrosine phosphorylation, due to IFN-α binding, of the IFNAR1/IFNAR2 receptor complex, by at least about 60%, or at least about 70%, preferably at least about 75%, more preferably at least about 80%; even more preferably at least about 85%, still more preferably at least about 90%, still more preferably at least about 95%, most preferably at least about 99%, as determined in the KIRA assay referenced above. In a particularly preferred embodiment, the neutralizing anti-IFN-α antibodies herein will be able to neutralize all, or substantially all, subtypes of IFN-α and will not be able to neutralize IFN-β. In this context, the term "substantially all" means that the neutralizing anti-IFN-α antibody will neutralize at least IFN-α1, IFN-α2, IFN-α4 IFN-α5, IFN-α8, IFN-α10, and IFN-α21.

For the purpose of the present invention, the ability of an anti-IFN-α antibody to block the binding of an IFN-α to receptor is defined as the property or capacity of a certain concentration of the antibody to reduce or eliminate the binding of IFN-α to IFNAR2 in a competition binding assay, as compared to the effect of an equivalent concentration of irrelevant control antibody on IFN-α binding to IFNAR2 in the assay. Preferably, the blocking anti-IFN-α antibody reduces the binding of IFN-α to IFNAR2 by at least about 50%, or at least about 55%, or at least about 60%, or at least about 65%, or at least about 70%, or at least about 75%, or at least about 80%, or at least about 85%, or at least about 90%, or at least about 95%, or at least about 99%, as compared to the irrelevant control antibody.

For the purpose of the present invention, the ability of an anti-IFN-α antibody to block the binding of IFN-α to IFNAR2 can be determined by a routine competition assay such as that described in *Antibodies: A Laboratory Manual*, Cold Spring Harbor Laboratory, Ed Harlow and David Lane (1988). For example, the IFN-α-binding ELISA assay described in Example 2 below could be modified to employ competition binding between an anti-IFN-α antibody and a soluble IFNAR2. Such an assay could be performed by layering the IFN-α on microtiter plates, incubating the layered plates with serial dilutions of unlabeled anti-IFN-α antibody or unlabeled control antibody admixed with a selected concentration of labeled IFNAR2 ECD-human IgG Fc fusion protein, detecting and measuring the signal in each incubation mixture, and then comparing the signal measurements exhibited by the various dilutions of antibody.

In a particularly preferred embodiment, the blocking anti-IFN-α antibodies herein will be able to block the IFNAR2-binding of all, or substantially all, subtypes of IFN-α and will not cross-react with IFN-β. In this context, the term "substantially all" means that the blocking anti-IFN-α antibody will block the IFNAR2-binding of at least IFN-α1, IFN-α2, IFN-α4, IFN-α5, IFN-α8, IFN-α10, and IFN-α21. In a particularly preferred embodiment, the blocking anti-IFN-α antibodies of the present invention will block the IFNAR2-binding of all known subtypes of IFN-α.

The term "epitope" is used to refer to binding sites for (monoclonal or polyclonal) antibodies on protein antigens.

Antibodies which bind to a particular epitope can be identified by "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. Competition assays are discussed above and below. According to the gene fragment expression assays, the open reading frame encoding the protein is fragmented either randomly or by specific genetic constructions and the reactivity of the expressed fragments of the protein with the antibody to be tested is determined. The gene fragments may, for example, be produced by PCR and then transcribed and translated into protein in vitro, in the presence of radioactive amino acids. The binding of the antibody to the radioactively labeled protein fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. The latter approach is suitable to define linear epitopes of about 5 to 15 amino acids.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels.

The term amino acid or amino acid residue, as used herein, refers to naturally occurring L amino acids or to D amino acids as described further below with respect to variants. The commonly used one- and three-letter abbreviations for amino acids are used herein (Bruce Alberts et al., Molecular Biology of the Cell, Garland Publishing, Inc., New York (3d ed. 1994)).

"Percent (%) amino acid sequence identity" with respect to the polypeptide sequences referred to herein is defined as the percentage of amino acid residues in a candidate sequence that are identical with the amino acid residues in a sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. and its source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif., and the source code for the ALIGN-2 program and instructions for its use are disclosed in International Application Publication No. WO2000/39297 published Jul. 6, 2000. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described above using the ALIGN-2 sequence comparison computer program. However, % amino acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "disease state" refers to a physiological state of a cell or of a whole mammal in which an interruption, cessation, or disorder of cellular or body functions, systems, or organs has occurred.

The term "effective amount" refers to an amount of a drug effective to treat (including prevention) of a disease, disorder or unwanted physiological conditions in a mammal. In the present invention, an "effective amount" of an anti-IFN-α antibody may reduce, slow down or delay an autoimmune disorder such as IDDM or SLE; reduce, prevent or inhibit (i.e., slow to some extent and preferably stop) the development of an autoimmune disorder such as IDDM or SLE; and/or relieve to some extent one or more of the symptoms associated with autoimmune disorders such as IDDM or SLE.

In the methods of the present invention, the term "control" and grammatical variants thereof, are used to refer to the prevention, partial or complete inhibition, reduction, delay or slowing down of an unwanted event, e.g. physiological condition, such as the generation of autoreactive T cells and development of autoimmunity.

"Treatment" refers to both therapeutic treatment and prophylactic or preventative measures. Those in need of treatment include those already with the disorder as well as those prone to have the disorder or those in which the disorder is to be prevented. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

"Pharmaceutically acceptable" carriers, excipients, or stabilizers are ones which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins;

chelating agents such as EDTA; sugar alcohols such as mannitol or sorbitol; salt-forming counterions such as sodium; and/or nonionic surfactants such as Tween™, polyethylene glycol (PEG), and Pluronics™.

"Mammal" for purposes of treatment refers to any animal classified as a mammal, including humans, domestic and farm animals, and zoo, sports, or pet animals, such as dogs, horses, cats, cows, etc. Preferably, the mammal is human.

B. Methods for Carrying Out the Invention

1. Generation of Antibodies
(i) Polyclonal Antibodies

Methods of preparing polyclonal antibodies are known in the art. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. It may be useful to conjugate the immunizing agent to a protein known to be immunogenic in the mammal being immunized, such as serum albumin, or soybean trypsin inhibitor. Examples of adjuvants which may be employed include Freund's complete adjuvant and MPL-TDM.

In another preferred embodiment, animals are immunized with a mixture of various, preferably all, IFN-α subtypes in order to generate anti-IFN-α antibodies with broad reactivity against IFN-α subtypes. In another preferred embodiment, animals are immunized with the mixture of human IFN-α subtypes that is present in the human lymphoblastoid interferons secreted by Burkitt lymphoma cells (Namalva cells) induced with Sendai virus, as described in Example 1 below. A suitable preparation of such human lymphoblastoid interferons can be obtained commercially (Product No. I-9887) from Sigma Chemical Company, St. Louis, Mo.

(ii) Monoclonal Antibodies

Monoclonal antibodies may be made using the hybridoma method first described by Kohler et al., *Nature* 256: 495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103, [Academic Press, 1996]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and MC.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.* 133: 3001 (1984); Brodeur et al., *Monoclonal Antibody Production Techniques and Applications*, pp. 51-63, Marcel Dekker, Inc., New York, [1987]).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis of Munson et al., *Anal. Biochem.* 107: 220 (1980).

After hybridoma cells are identified that produce antibodies of the desired specificity, affinity, and/or activity, the cells may be subcloned by limiting dilution procedures and grown by standard methods (Goding, *Monoclonal Antibodies: Principles and Practice*, pp. 59-103, Academic Press, 1996). Suitable culture media for this purpose include, for example, DMEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (Morrison, et al., *Proc. Nat. Acad. Sci.* 81: 6851 [1984]), or by covalently joining to the immunoglobulin coding sequence all or part of the coding sequence for a non-immunoglobulin polypeptide. In that manner, "chimeric" or "hybrid" antibodies are prepared that have the binding specificity of an anti-IFN-α monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for an IFN-α and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

Recombinant production of antibodies will be described in more detail below.

(iii) Humanized Antibodies

Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers by substituting rodent CDRs or CDR sequences for the corresponding sequences of a human antibody (Jones et al., *Nature* 321: 522-525 [1986]; Riechmann et al., *Nature* 332: 323-327 [1988]; Verhoeyen et al., *Science* 239: 1534-1536 [1988]); reviewed in Clark, *Immunol. Today* 21: 397-402 [2000]).

Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details, see U.S. Pat. No. 5,821,337.

(iv) Human Antibodies

Attempts to use the same technology for generating human mAbs have been hampered by the lack of a suitable human myeloma cell line. The best results were obtained using heteromyelomas (mouse×human hybrid myelomas) as fusion partners (Kozbor, *J. Immunol.* 133: 3001 (1984); Brodeur, et al., *Monoclonal Antibody Production Techniques and Applications*, pp. 51-63, Marcel Dekker, Inc., New York, 1987). Alternatively, human antibody-secreting cells can be immortalized by infection with the Epstein-Barr virus (EBV). However, EBV-infected cells are difficult to clone and usually produce only relatively low yields of immunoglobulin (James and Bell, *J. Immunol. Methods* 100: 5-40 [1987]). In future, the immortalization of human B cells might possibly be achieved by introducing a defined combination of transforming genes. Such a possibility is highlighted by a recent demonstration that the expression of the telomerase catalytic subunit together with the SV40 large T oncoprotein and an oncogenic allele of H-ras resulted in the tumorigenic conversion of normal human epithelial and fibroblast cells (Hahn et al., *Nature* 400: 464-468 [1999]).

It is now possible to produce transgenic animals (e.g. mice) that are capable, upon immunization, of producing a repertoire of human antibodies in the absence of endogenous immunoglobulin production (Jakobovits et al., *Nature* 362: 255-258 [1993]; Lonberg and Huszar, *Int. Rev. Immunol.* 13: 65-93 [1995]; Fishwild at al., *Nat. Biotechnol.* 14: 845-851 [1996]; Mendez et al., *Nat. Genet.* 15: 146-156 [1997]; Green, *J. Immunol. Methods* 231: 11-23 [1999]; Tomizuka et al., *Proc. Natl. Acad. Sci. USA* 97: 722-727 [2000]; reviewed in Little at al., *Immunol. Today* 21: 364-370 [2000]). For example, it has been described that the homozygous deletion of the antibody heavy chain joining region ($J_H$) gene in chimeric and germ-line mutant mice results in complete inhibition of endogenous antibody production (Jakobovits et al., *Proc. Natl. Acad. Sci. USA* 90: 2551-2555 [1993]). Transfer of the human germ-line immunoglobulin gene array in such germ-line mutant mice results in the production of human antibodies upon antigen challenge (Jakobovits et al., *Nature* 362: 255-258 [1993]).

Mendez et al. (*Nature Genetics* 15: 146-156 [1997]) have generated a line of transgenic mice designated as "XenoMouse® II" that, when challenged with an antigen, generates high affinity fully human antibodies. This was achieved by germ-line integration of megabase human heavy chain and light chain loci into mice with deletion into endogenous $J_H$ segment as described above. The XenoMouse® II harbors 1,020 kb of human heavy chain locus containing approximately 66 $V_H$ genes, complete $D_H$ and $J_H$ regions and three different constant regions (μ, δ and γ), and also harbors 800 kb of human κ locus containing 32 Vκ genes, Jκ segments and Cκ genes. The antibodies produced in these mice closely resemble that seen in humans in all respects, including gene rearrangement, assembly, and repertoire. The human antibodies are preferentially expressed over endogenous antibodies due to deletion in endogenous $J_H$ segment that prevents gene rearrangement in the murine locus.

Tomizuka et al. (*Proc. Natl. Acad. Sci. USA* 97: 722-727 [2000]) have recently described generation of a double transchromosomic (Tc) mice by introducing two individual human chromosome fragments (hCFs), one containing the entire Ig heavy chain locus (IgH, ~1.5 Mb) and the other the entire κ light chain locus (Igκ, ~2 Mb) into a mouse strain whose endogenous IgH and Igκ loci were inactivated. These mice mounted antigen-specific human antibody response in the absence of mouse antibodies. The Tc technology may allow for the humanization of over megabase-sized, complex loci or gene clusters (such as those encoding T-cell receptors, major histocompatibility complex, P450 cluster etc) in mice or other animals. Another advantage of the method is the elimination of a need of cloning the large loci. This is a significant advantage since the cloning of over megabase-sized DNA fragments encompassing whole Ig loci remains difficult even with the use of yeast artificial chromosomes (Peterson et al., *Trends Genet.* 13: 61-66 [1997]; Jacobovits, *Curr. Biol.* 4: 761-763 [1994]). Moreover, the constant region of the human IgH locus is known to contain sequences difficult to clone (Kang and Cox, *Genomics* 35: 189-195 [1996]).

Alternatively, the phage display technology can be used to produce human antibodies and antibody fragments in vitro, from immunoglobulin variable (V) domain gene repertoires from unimmunized donors (McCafferty et al., *Nature* 348: 552-553 [1990]; reviewed in Kipriyanov and Little, *Mol. Biotechnol.* 12: 173-201 [1999]; Hoogenboom and Chames, *Immunol. Today* 21: 371-378 [2000]). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats (reviewed in Johnson and Chiswell, *Current Opinion in Structural Biology* 3: 564-571 [1993)]; Winter et al., *Annu. Rev. Immunol.* 12: 433-455 [1994]; Dall'Acqua and Carter, *Curr. Opin. Struct. Biol.* 8: 443-450 [1998]; Hoogenboom and Chames, *Immunol. Today* 21: 371-378 [2000]). Several sources of V-gene segments can be used for phage display. Clackson et al., (*Nature* 352: 624-628 [1991]) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222: 581-597 (1991), or Griffiths et al., *EMBO J.* 12: 725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., *Bio/Technol.* 10: 779-783 [1992]). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires (also known as "the mother-of-all libraries") has been described by Waterhouse et al., *Nucl. Acids Res.* 21: 2265-2266 (1993), and the isolation of a high affinity human antibody directly from such large phage library is reported by Griffiths et al., *EMBO J.* 13: 3245-3260 (1994). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213, published 1 Apr. 1993). Unlike traditional humanization of rodent antibodies by CDR grafting, this technique provides completely human antibodies, which have no framework or CDR residues of rodent origin.

(v) Bispecific Antibodies

Bispecific antibodies are monoclonal, preferably human or humanized, antibodies that have binding specificities for at least two different antigens. In the present case, one of the binding specificities is for an IFN-α to provide a neutralizing antibody, the other one is for any other antigen.

Methods for making bispecific antibodies are known in the art. Traditionally, the recombinant production of bispecific antibodies is based on the co-expression of two immunoglobulin heavy chain-light chain pairs, where the two heavy chains have different specificities (Millstein and Cuello, *Nature* 305: 537-539 [1983]). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published 13 May 1993), and in Traunecker et al., *EMBO J.* 10: 3655-3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one aim, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation.

For further details of generating bispecific antibodies see, for example, Suresh et al., *Methods in Enzymology* 121, 210 (1986).

(vi) Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

(vii) Antibody Fragments

In certain embodiments, the neutralizing anti-IFN-α antibody (including murine, human and humanized antibodies, and antibody variants) is an antibody fragment. Various techniques have been developed for the production of antibody fragments. Traditionally, these fragments were derived via proteolytic digestion of intact antibodies (see, e.g., Morimoto et al., *J. Biochem. Biophys. Methods* 24:107-117 [1992] and Brennan et al., *Science* 229:81 [1985]). However, these fragments can now be produced directly by recombinant host cells (reviewed in Hudson, *Curr. Opin. Immunol.* 11: 548-557 [1999]; Little et al., *Immunol. Today* 21: 364-370 [2000]). For example, Fab'-SH fragments can be directly recovered from E. coli and chemically coupled to form F(ab')₂ fragments (Carter et al., Bio/Technology 10:163-167 [1992]). In another embodiment, the F(ab')₂ is formed using the leucine zipper GCN4 to promote assembly of the F(ab')₂ molecule. According to another approach, Fv, Fab or F(ab')₂ fragments can be isolated directly from recombinant host cell culture. Other techniques for the production of antibody fragments will be apparent to the skilled practitioner.

(viii) Amino Acid Sequence Variants of Antibodies

Amino acid sequence modification(s) of the anti-IFN-α antibodies described herein are contemplated. For example, it may be desirable to improve the binding affinity and/or other biological properties of the antibody. Amino acid sequence variants of the anti-IFN-α antibodies are prepared by introducing appropriate nucleotide changes into the nucleic acid encoding the anti-IFN-α antibody chains, or by peptide synthesis. Such modifications include, for example, deletions from, and/or insertions into and/or substitutions of, residues within the amino acid sequences of the anti-IFN-α antibody. Any combination of deletion, insertion, and substitution is made to arrive at the final construct, provided that the final construct possesses the desired characteristics. The amino acid changes also may alter post-translational processes of the anti-IFN-α antibody, such as changing the number or position of glycosylation sites.

A useful method for identification of certain residues or regions of the neutralizing anti-IFN-α antibody that are preferred locations for mutagenesis is called "alanine scanning mutagenesis," as described by Cunningham and Wells *Science,* 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-IFN-α antibody variants are screened for the desired activity.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an anti-IFN-α neutralizing antibody with an N-terminal methionyl residue or the antibody fused to an epitope tag. Other insertional variants of the anti-IFN-α antibody molecule include the fusion to the N- or C-terminus of the antibody of an enzyme or a polypeptide which increases the serum half-life of the antibody.

Another type of variant is an amino acid substitution variant. These variants have at least one amino acid residue in the neutralizing anti-IFN-α antibody molecule removed and a different residue inserted in its place. The sites of greatest interest for substitution mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another class.

Any cysteine residue not involved in maintaining the proper conformation of the neutralizing anti-IFN-α antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as a Fv fragment).

A particularly preferred type of substitution variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitution variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. antagonist activity) as herein disclosed. In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and IFN-α. Such contact residues and neighboring residues are candidates for substitution according to the techniques elaborated herein. Once such variants are generated, the panel of variants is subjected to screening as described herein and antibodies with superior properties in one or more relevant assays may be selected for further development.

(ix) Glycosylation Variants

Antibodies are glycosylated at conserved positions in their constant regions (Jefferis and Lund, *Chem. Immunol.* 65:111-128 [1997]; Wright and Morrison, *Trends Biotechnol.* 15:26-32 [1997]). The oligosaccharide side chains of the immunoglobulins affect the protein's function (Boyd et al., *Mol. Immunol.* 32:1311-1318 [1996]; Wittwe and Howard, *Biochem.* 29:4175-4180 [1990]), and the intramolecular interaction between portions of the glycoprotein which can affect the conformation and presented three-dimensional surface of the glycoprotein (Jefferis and Lund, supra; Wyss and Wagner, *Current Opin. Biotech.* 7:409-416 [1996]). Oligosaccharides may also serve to target a given glycoprotein to certain molecules based upon specific recognition structures. For example, it has been reported that in agalactosylated IgG, the oligosaccharide moiety 'flips' out of the inter-CH2 space and terminal N-acetylglucosamine residues become available to bind mannose binding protein (Malhotra et al., *Nature Med.* 1:237-243 [1995]). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., *Mol. Immunol.* 32:1311-1318 [1996]), while selective removal of sialic acid residues using neuraminidase resulted in no loss of DMCL. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., *Mature Biotech.* 17:176-180 [1999]).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), the extent of glycosylation, etc.

Addition of glycosylation sites to the antibody is conveniently accomplished by altering the amino acid sequence such that it contains one or more of the above-described tripeptide sequences (for N-linked glycosylation sites). The alteration may also be made by the addition of or substitution by, one or more serine or threonine residues to the sequence of the original antibody (for O-linked glycosylation sites). Similarly, removal of glycosylation sites can be accomplished by amino acid alteration within the native glycosylation sites of the antibody.

The amino acid sequence is usually altered by altering the underlying nucleic acid sequence. Nucleic acid molecules encoding amino acid sequence variants of the anti-IFN-α antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-IFN-α antibody.

The glycosylation (including glycosylation pattern) of antibodies may also be altered without altering the amino acid sequence or the underlying nucleotide sequence. Glycosylation largely depends on the host cell used to express the antibody. Since the cell type used for expression of recombinant glycoproteins, e.g. antibodies, as potential therapeutics is rarely the native cell, significant variations in the glycosylation pattern of the antibodies can be expected (see, e.g. Hse et al., *J. Biol. Chem.* 272:9062-9070 [1997]). In addition to the choice of host cells, factors which affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5.278,299). Glycosylation, or certain types of glycosylation, can be enzymatically removed from the glycoprotein, for example using endoglycosidase H (Endo H). In addition, the recombinant host cell can be genetically engineered, e.g. make defective in processing certain types of polysaccharides. These and similar techniques are well known in the art.

The glycosylation structure of antibodies can be readily analyzed by conventional techniques of carbohydrate analysis, including lectin chromatography, NMR, Mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-β-galactosidase), elimination using harsh alkaline environment to release mainly O-linked structures, and chemical methods using anhydrous hydrazine to release both N- and O-linked oligosaccharides.

(x) Other Modifications of Antibodies

The neutralizing anti-IFN-α antibodies disclosed herein may also be formulated as immunoliposomes. Liposomes containing the antibody are prepared by methods known in the art, such as described in Epstein et al., *Proc. Natl. Acad. Sci. USA* 82:3688 (1985); Hwang et al., *Proc. Natl Acad. Sci. USA* 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent (such as Doxorubicin) is optionally contained within the liposome. See Gabizon et al., *J. National Cancer Inst.* 81(19):1484 (1989).

The antibody of the present invention may also be used in ADEPT by conjugating the antibody to a prodrug-activating enzyme which converts a prodrug (e.g., a peptidyl chemotherapeutic agent, see WO81/01145) to an active drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active form exhibiting the desired biological properties.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328:457-458 (1987)). Antibody-abzyme conjugates can be prepared as described herein for delivery of the abzyme to a desired cell population.

The enzymes can be covalently bound to the neutralizing anti-IFN-α antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature* 312:604-608 [1984]).

In certain embodiments of the invention, it may be desirable to use an antibody fragment, rather than an intact antibody. In this case, it may be desirable to modify the antibody fragment in order to increase its serum half-life. This may be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis). See WO96/32478 published Oct. 17, 1996.

The salvage receptor binding epitope generally constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment.

Covalent modifications of the neutralizing anti-IFN-α antibodies are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues. Exemplary covalent modifications of polypeptides are described in U.S. Pat. No. 5,534,615, specifically incorporated herein by reference. A preferred type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

2. Screening for Antibodies with the Desired Properties

Techniques for generating antibodies have been described above. Anti-IFN-α antibodies with the desired, broad range neutralizing properties can then be identified by methods known in the art.

(i) Binding Assays

Thus, for example, the neutralizing anti-IFN-α antibodies of the present invention can be identified in IFN-α binding assays, by incubating a candidate antibody with one or more individual IFN-α subtypes, or an array or mixture of various IFN-α subtypes, and monitoring binding and neutralization of a biological activity of IFN-α. The binding assay may be performed with purified IFN-α polypeptide(s). In one embodiment, the binding assay is a competitive binding assay, where the ability of a candidate antibody to compete with a known anti-IFN-α antibody for IFN-α binding is evaluated. The assay may be performed in various formats, including the ELISA format, also illustrated in the Examples below. IFN-α binding of a candidate antibody may also be monitored in a BIAcore™ Biosensor assay, as described below.

Any suitable competition binding assay known in the art can be used to characterize the ability of a candidate anti-IFN-α monoclonal antibody to compete with murine anti-human IFN-α monoclonal antibody 9F3 for binding to a particular IFN-α species. A routine competition assay is described in *Antibodies: A Laboratory Manual*, Cold Spring Harbor Laboratory, Ed Harlow and David Lane (1988). In another embodiment, the IFN-α-binding ELISA assay described in Example 2 below could be modified to employ IFN-α binding competition between a candidate antibody and the 9F3 antibody. Such an assay could be performed by layering the IFN-α on microtiter plates, incubating the layered plates with serial dilutions of unlabeled anti-IFN-α antibody or unlabeled control antibody admixed with a selected concentration of labeled 9F3 antibody, detecting and measuring the signal from the 9F3 antibody label, and then comparing the signal measurements exhibited by the various dilutions of antibody.

(ii) Antiviral Assays

The ability of a candidate antibody to neutralize a biological activity of IFN-α can, for example, be carried out by monitoring the neutralization of the antiviral activity of IFN-α as described by Kawade, *J. Interferon Res.* 1:61-70 (1980), or Kawade and Watanabe, *J. Interferon Res.* 4:571-584 (1984). Briefly, a fixed concentration of IFN-α premixed with various dilutions of a candidate antibody is added to human amnion-derived FL cells, and the ability of the candidate antibody to neutralize the antiviral activity of IFN-α is determined, using an appropriate virus, e.g. Sindbis virus. The titers are expressed in international units (IU), as determined with the international reference human IFN-α (NIH Ga23-901-527).

The candidate anti-IFN-α antibody is considered able to inhibit the anti-viral activity of a selected IFN-α subtype if a certain concentration of the antibody inhibits more anti-viral activity than the baseline level of anti-viral activity inhibition measured in the presence of an equivalent concentration of control antibody. Optionally, the certain concentration of the candidate anti-IFN-α antibody will inhibit at least or about 60%, or at least or about 70%, preferably at least or about 75%, or more preferably at least or about 80%, or even more preferably at least or about 85%, or still more preferably at least or about 90%, or still more preferably at least or about 95%, or most preferably at least or about 99% of the anti-viral activity of the selected IFN-α subtype in the anti-viral activity assay as compared to baseline activity measured in the presence of an equivalent concentration of control antibody. The candidate anti-IFN-α antibody is considered unable to inhibit the anti-viral activity of a selected IFN-α subtype if there is no concentration of the antibody that exhibits more anti-viral activity inhibition than the baseline level of anti-viral activity inhibition measured in the presence of an equivalent concentration of control antibody.

In a preferred embodiment, each interferon species used in the viral infectivity assay is titrated to a concentration that provides the same level of inhibition of viral growth as that induced by a preselected number of units of an IFN-α standard. This concentration serves to provide the normalized units of the subject interferon species. In order to assess the ability of an anti-IFN-α antibody to inhibit the anti-viral activity of various IFN-α subtypes, the effective concentration (EC50) of anti-IFN-α antibody for inhibiting 50% of a particular IFN-α subtype's anti-viral activity (at the concentration titrated to provide the normalized units of activity) is determined for each IFN-α subtype to be tested.

In one embodiment, the antiviral activity neutralization assay is performed as described in Example 1 below. Briefly, A549 cells are grown to a density of $5\times10^5$ A549 cells/well on 96-well microtiter plates. Serial dilutions of candidate anti-IFN-α antibody are incubated with 0.2 units/μl of a selected IFN-α subtype (normalized to 0.2 units/μl of NIH reference standard recombinant human IFN-α2) in a total volume of 100 μl at 37° C. for one hour. Each 100 μl volume of antibody/interferon incubation mixture is then added to $5\times10^5$ A549 cells and 100 μl of culture medium in an individual well on the microliter plate, yielding a final IFN-α concentration of 100 units/ml in each well. The resulting cell culture mixtures are incubated for 24 hours at 37° C. Cells are then challenged with $2\times10^5$ pfu of encephalomyocarditis (EMC) virus and incubated for an additional 24 hours at 37° C. At the end of the incubation, cell viability is determined by visual microscopic examination or crystal violet staining. The effective concentration (EC50) of a candidate IFN-α antibody for inhibiting 50% of a particular IFN-α subtype's anti-viral activity in the assay is determined for each IFN-α subtype to be tested.

In one aspect of the invention, the anti-IFN-α antibody that exhibits anti-viral activity neutralization against the subject IFN-α subtypes will exhibit an EC50 of up to or about 20 μg/ml, or up to or about 10 μg/ml, or up to or about 5 μg/ml, or up to or about 4 μg/ml, or up to or about 3 μg/ml, or up to or about 2 μg/ml, or up to or about 1 μg/ml with respect to each of the subject IFN-α subtypes in the A549 cell EMC viral inhibition assay described above.

In another aspect of the invention, the anti-IFN-α antibody that exhibits anti-viral activity neutralization against the subject IFN-α subtypes will exhibit an EC50 from or about 0.1 μg/ml to or about 20 μg/ml, from or about 0.1 μg/ml to or about 10 μg/ml, from or about 0.1 μg/ml to or about 5 μg/ml, or from or about 0.1 μg/ml to or about 4 μg/ml, from or about 0.1 μg/ml to or about 3 μg/ml, from or about 0.1 μg/ml to or about 2 μg/ml, or from or about 0.1 μg/ml to or about 1 μg/ml with respect to each of the subject IFN-α subtypes in the A549 cell EMC viral inhibition assay described above.

In another aspect of the invention, the anti-IFN-α antibody that anti-viral activity neutralization against the subject IFN-α subtypes will exhibit an EC50 from or about 0.2 μg/ml to or about 20 μg/ml, from or about 0.2 μg/ml to or about 10 μg/ml, from or about 0.2 μg/ml to or about 5 μg/ml, or from or about 0.2 μg/ml to or about 4 μg/ml, from or about 0.2 μg/ml to or about 3 μg/ml, from or about 0.2 μg/ml to or about 2 μg/ml, or from or about 0.2 μg/ml to or about 1 μg/ml with respect to each of the subject IFN-α subtypes in the A549 cell EMC viral inhibition assay described above.

In another aspect of the invention, the anti-IFN-α antibody that neutralizes the anti-viral activity of the subject IFN-α subtypes will exhibit an EC50 from or about 0.3 μg/ml to or about 20 μg/ml, from or about 0.3 μg/ml to or about 10 μg/ml, from or about 0.3 μg/ml to or about 5 μg/ml, or from or about 0.3 μg/ml to or about 4 μg/ml, from or about 0.3 μg/ml to or about 3 μg/ml, from or about 0.3 μg/ml to or about 2 μg/ml, or from or about 0.3 μg/ml to or about 1 μg/ml with respect to each of the subject IFN-α subtypes in the A549 cell EMC viral inhibition assay described above.

In another aspect of the invention, the anti-IFN-α antibody that neutralizes the anti-viral activity of the subject IFN-α subtypes will exhibit an EC50 from or about 0.4 μg/ml to or about 20 μg/ml, from or about 0.4 μg/ml to or about 10 μg/ml, from or about 0.4 μg/ml to or about 5 μg/ml, or from or about 0.4 μg/ml to or about 4 μg/ml, from or about 0.4 μg/ml to or about 3 μg/ml, from or about 0.4 μg/ml to or about 2 μg/ml, or from or about 0.4 μg/ml to or about 1 μg/ml with respect to each of the subject IFN-α subtypes in the A549 cell EMC viral inhibition assay described above.

In another aspect of the invention, the anti-IFN-α antibody that neutralizes the anti-viral activity of the subject IFN-α subtypes will exhibit an EC50 from or about 0.5 μg/ml to or about 20 μg/ml, from or about 0.5 μg/ml to or about 10 μg/ml, from or about 0.5 μg/ml to or about 5 μg/ml, or from or about 0.5 μg/ml to or about 4 μg/ml, from or about 0.5 μg/ml to or about 3 μg/ml, from or about 0.5 μg/ml to or about 2 μg/ml, or from or about 0.5 μg/ml to or about 1 μg/ml with respect to each of the subject IFN-α subtypes in the A549 cell EMC viral inhibition assay described above.

In another aspect of the invention, the anti-IFN-α antibody that neutralizes the anti-viral activity of the subject IFN-α subtypes will exhibit an EC50 from or about 0.6 μg/ml to or about 20 μg/ml, from or about 0.6 μg/ml to or about 10 μg/ml, from or about 0.6 μg/ml to or about 5 μg/ml, or from or about 0.6 μg/ml to or about 4 μg/ml, from or about 0.6 μg/ml to or about 3 μg/ml, from or about 0.6 μg/ml to or about 2 μg/ml, or from or about 0.6 μg/ml to or about 1 μg/ml with respect to each of the subject IFN-α subtypes in the A549 cell EMC viral inhibition assay described above.

In another aspect of the invention, the anti-IFN-α antibody that neutralizes the anti-viral activity of the subject IFN-α subtypes will exhibit an EC50 from or about 0.7 μg/ml to or about 20 μg/ml, from or about 0.7 μg/ml to or about 10 μg/ml, from or about 0.7 μg/ml to or about 5 μg/ml, or from or about 0.7 μg/ml to or about 4 μg/ml, from or about 0.7 μg/ml to or about 3 μg/ml, from or about 0.7 μg/ml to or about 2 μg/ml, or from or about 0.7 μg/ml to or about 1 μg/ml with respect to each of the subject IFN-α subtypes in the A549 cell EMC viral inhibition assay described above.

In another aspect of the invention, the anti-IFN-α antibody that neutralizes the anti-viral activity of the subject IFN-α subtypes will exhibit an EC50 from or about 0.8 μg/ml to or about 20 μg/ml, from or about 0.8 μg/ml to or about 10 μg/ml, from or about 0.8 μg/ml to or about 5 μg/ml, or from or about 0.8 μg/ml to or about 4 μg/ml, from or about 0.8 μg/ml to or about 3 μg/ml, from or about 0.8 μg/ml to or about 2 μg/ml, or from or about 0.8 μg/ml to or about 1 μg/ml with respect to each of the subject IFN-α subtypes in the A549 cell EMC viral inhibition assay described above.

In another aspect of the invention, the anti-IFN-α antibody that neutralizes the anti-viral activity of the subject IFN-α subtypes will exhibit an EC50 from or about 0.9 μg/ml to or about 20 μg/ml, from or about 0.9 μg/ml to or about 10 μg/ml, from or about 0.9 μg/ml to or about 5 μg/ml, or from or about 0.9 μg/ml to or about 4 μg/ml, from or about 0.9 μg/ml to or about 3 μg/ml, from or about 0.9 μg/ml to or about 2 μg/ml, or from or about 0.9 μg/ml to or about 1 μg/ml with respect to each of the subject IFN-α subtypes in the A549 cell EMC viral inhibition assay described above.

In another aspect of the invention, the anti-IFN-α antibody that neutralizes the anti-viral activity of the subject IFN-α subtypes will exhibit an EC50 from or about 1 μg/ml to or about 20 μg/ml, from or about 1 μg/ml to or about 10 μg/ml, from or about 1 μg/ml to or about 5 μg/ml, or from or about 1 μg/ml to or about 4 μg/ml, from or about 1 μg/ml to or about 3 μg/ml, or from or about 1 μg/ml to or about 2 μg/ml with respect to each of the subject IFN-α subtypes in the A549 cell EMC viral inhibition assay described above.

(iii) Cross-Blocking Assays

To screen for antibodies which bind to an epitope on IFN-α bound by an antibody of interest, a routine cross-blocking assay such as that described in *Antibodies, A Laboratory Manual*, Cold Spring Harbor Laboratory, Ed Harlow and David Lane (1988), can be performed. Alternatively, or additionally, epitope mapping can be performed by methods known in the art. For example, the IFN-α epitope bound by a monoclonal antibody of the present invention can be determined by competitive binding analysis as described in Fendly et al. *Cancer Research* 50:1550-1558 (1990). In another example, cross-blocking studies can be done with direct fluorescence on microtiter plates. In this method, the monoclonal antibody of interest is conjugated with fluorescein isothiocyanate (FITC), using established procedures (Wofsy et al. *Selected Methods in Cellular Immunology*, p. 287, Mishel and Schiigi (eds.) San Francisco: W.J. Freeman Co. (1980)). The selected IFN-α is layered onto the wells of microtiter plates, the layered wells are incubated with mixtures of (1) FITC-labeled monoclonal antibody of interest and (2) unlabeled test monoclonal antibody, and the fluorescence in each well is quantitated to determine the level of cross-blocking exhibited by the antibodies. Monoclonal antibodies are considered to share an epitope if each blocks binding of the other by 50% or greater in comparison to an irrelevant monoclonal antibody control.

The results obtained in the cell-based biological assays can then be followed by testing in animal, e.g. murine, models, and human clinical trials. If desired, murine monoclonal antibodies identified as having the desired properties can be converted into chimeric antibodies, or humanized by techniques well known in the art, including the "gene conversion mutagenesis" strategy, as described in U.S. Pat. No. 5,821,337, the entire disclosure of which is hereby expressly incorporated by reference. Humanization of a particular anti-IFN-α antibody herein is also described in the Examples below.

(iv) Phage Display Method

Anti-IFN-α antibodies of the invention can be identified by using combinatorial libraries to screen for synthetic antibody clones with the desired activity or activities. In principle, synthetic antibody clones are selected by screening phage libraries containing phage that display various fragments (e.g. Fab, $F(ab')_2$, etc.) of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-IFN-α antibodies of the invention can be obtained by designing a suitable antigen screening procedure to select for the phage clone of interest followed by construction of a full length anti-IFN-α antibody clone using the Fv sequences from the phage clone of interest and suitable constant region (Fc) sequences described in Kabat et al. (1991), supra.

Construction of Phage Display Libraries

The antigen-binding domain of an antibody is formed from two variable (V) regions of about 110 amino acids each, from the light (VL) and heavy (VH) chains, that both present three hypervariable loops or complementarity-determining regions (CDRs). Variable domains can be displayed functionally on phage, either as single-chain Fv (scFv) fragments, in which VH and VL are covalently linked through a short, flexible peptide, or as or $D(ab')_2$ fragments, in which they are each fused to a constant domain and interact non-covalently, as described in Winter et al., *Ann. Rev. Immunol.,* 12: 433-455 (1994). As used herein, scFv encoding phage clones and Fab or $F(ab')_2$ encoding phage clones are collectively referred to as "Fv phage clones" or "Fv clones".

The naive repertoire of an animal (the repertoire before antigen challenge) provides it with antibodies that can bind with moderate affinity ($K_d^{-1}$ of about $10^6$ to $10^7$ $M^{-1}$) to essentially any non-self molecule. The sequence diversity of antibody binding sites is not encoded directly in the germline but is assembled in a combinatorial manner from V gene segments. In human heavy chains, the first two hypervariable loops (H1 and H2) are drawn from less than 50 VH gene segments, which are combined with D segments and JH segments to create the third hypervariable loop (H3). In human light chains, the first two hypervariable loops (L1 and L2) and much of the third (L3) are drawn from less than approximately 30 Vλ and less than approximately 30 Vκ segments to complete the third hypervariable loop (L3).

Each combinatorial rearrangement of V-gene segments in stem cells gives rise to a B cell that expresses a single VH-VL combination. Immunizations triggers any B cells making a combination that binds the immunogen to proliferate (clonal expansion) and to secrete the corresponding antibody. These naive antibodies are then matured to high affinity ($K_d^{-1}$ of $10^9$-$10^{10}$ $M^{-1}$) by a process of mutagenesis and selection known as affinity maturation. It is after this point that cells are normally removed to prepare hybridomas and generate high-affinity monoclonal antibodies.

At three stages of this process, repertoires of VH and VL genes can be separately cloned by polymerase chain reaction (PCR) and recombined randomly in phage libraries, which can then be searched for antigen-binding clones as described in Winter et al., *Ann. Rev. Immunol.,* 12: 433-455 (1994).

Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V- or VIII-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

Phage display mimics the B cell. Filamentous phage is used to display antibody fragments by fusion to the minor coat protein pIII The antibody fragments can be displayed as single chain Fv fragments, in which VH and VL domains are connected on the same polypeptide chain by a flexible polypeptide spacer, e.g. as described by Marks et al., *J. Mol. Biol.*, 222: 581-597 (1991), or as Fab (including F(ab')$_2$) fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.*, 19: 4133-4137 (1991). When antibody fragments are fused to the N-terminus of pIII, the phage is infective. However, if the N-terminal domain of pIII is excised and fusions made to the second domain, the phage is not infective, and wild type pIII must be provided by helper phage.

The pIII fusion and other proteins of the phage can be encoded entirely within the same phage replicon, or on different replicons. When two replicons are used, the pIII fusion is encoded on a phagemid, a plasmid containing a phage origin of replication. Phagemids can be packaged into phage particles by "rescue" with a helper phage such as M13K07 that provides all the phage proteins, including pIII, but due to a defective origin is itself poorly packaged in competitions with the phagemids as described in Vieira and Messing, *Meth. Enzymol.*, 153: 3-11 (1987). In a preferred method, the phage display system is designed such that the recombinant phage can be grown in host cells under conditions permitting no more than a minor amount of phage particles to display more than one copy of the Fv-coat protein fusion on the surface of the particle as described in Bass et al., *Proteins*, 8: 309-314 (1990) and in WO 92/09690 (PCT/US91/09133 published Jun. 11, 1992).

In general, nucleic acids encoding antibody gene fragments are obtained from immune cells harvested from humans or animals. If a library biased in favor of anti-IFN-α clones is desired, the subject is immunized with IFN-α to generate an antibody response, and spleen cells and/or circulating B cells other peripheral blood lymphocytes (PBLs) are recovered for library construction. In a preferred embodiment, a human antibody gene fragment library biased in favor of anti-human IFN-α clones is obtained by generating an anti-human IFN-α antibody response in transgenic mice carrying a functional human immunoglobulin gene array (and lacking a functional endogenous antibody production system) such that IFN-α immunization gives rise to B cells producing human-sequence antibodies against IFN-α.

In another preferred embodiment, animals are immunized with a mixture of various, preferably all, IFN-α subtypes in order to generate an antibody response that includes B cells producing anti-IFN-α antibodies with broad reactivity against IFN-α subtypes. In another preferred embodiment, animals are immunized with the mixture of human IFN-α subtypes that is present in the human lymphoblastoid interferons secreted by Burkitt lymphoma cells (Namalva cells) induced with Sendai virus, as described in Example 1 below. A suitable preparation of such human lymphoblastoid interferons can be obtained commercially (Product No. 1-9887) from Sigma Chemical Company, St. Louis, Mo.

Additional enrichment for anti-IFN-α reactive cell populations can be obtained by using a suitable screening procedure to isolate B cells expressing IFN-α-specific membrane bound antibody, e.g., by cell separation with IFN-α affinity chromatography or adsorption of cells to fluorochrome-labeled IFN-α followed by fluorescence-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which IFN-α is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci. (USA)*, 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature*, 341: 544-546 (1989). However, for amplifying from cDNA, back primers can also be based in the leader exon as described in Jones et al., *Biotechnol.*, 9: 88-89 (1991), and forward primers within the constant region as described in Sastry et al., *Proc. Natl. Acad. Sci. (USA)*, 86: 5728-5732 (1989). To maximize complementarity, degeneracy can be incorporated in the primers as described in Orlandi et al. (1989) or Sastry et al. (1989). Preferably, the library diversity is maximized by using PCR primers targeted to each V-gene family in order to amplify all available VH and VL arrangements present in the immune cell nucleic acid sample, e.g. as described in the method of Marks et al., *J. Mol. Biol.*, 222: 581-597 (1991) or as described in the method of Orum et al., *Nucleic Acids Res.*, 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature*, 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.*, 227: 776-798 (1992)), and mapped (reported in Matsuda et al., *Nature Genet.*, 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.*, 227: 381-388 (1992). VH repertoires can also be made with all the sequence diversity focussed in a long H3 loop of a single length as described in Barbas et al., *Proc. Natl. Acad. Sci. USA*, 89: 4457-4461 (1992). Human Vκ and Vλ segments have been cloned and sequenced (reported in Williams and Winter, *Eur. J. Immunol.*, 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.*, 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene*, 128: 119-126 (1993), or in vivo by combinatorial infection, e.g., the loxP system described in Waterhouse et al., *Nucl. Acids Res.*, 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g. as described in Barbas et al., *Proc. Natl. Acad. Sci. USA*, 88: 7978-7982 (1991), or assembled together by PCR and then cloned, e.g. as described in Clackson et al., *Nature*, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.*, 20: 3831-3837 (1992).

The antibodies produced by naive libraries (either natural or synthetic) can be of moderate affinity ($K_d^{-1}$ of about $10^6$ to $10^7$ M$^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., *Technique*, 1: 11-15 (1989)) in the method of Hawkins et al., *J. Mol. Biol.*, 226: 889-896 (1992) or in the method of Gram et al., *Proc. Natl. Acad. Sci USA*, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.*, 10: 779-783 (1992). This technique allows the production of antibodies and antibody fragments with affinities in the $10^{-9}$ M range.

Panning Phage Display Libraries for Anti-IFN-α Clones a. Synthesis of IFN-α

Nucleic acid sequence encoding the IFN-α subtypes used herein can be designed using published amino acid and nucleic acid sequences of interferons, e.g. see the *J. Interferon Res.*, 13: 443-444 (1993) compilation of references containing genomic and cDNA sequences for various type I interferons, and the references cited therein. For the IFN-αA (IFN-α2), IFN-αB (IFN-α8), IFN-αC (IFN-α10), IFN-αD (IFN-α1), IFN-αE (IFN-α22), IFN-αF (IFN-α21), IFN-αG (IFN-α5), and IFN-αH (IFN-α14) amino acid sequences or cDNA sequences, see FIGS. 3 and 4 on pages 23-24 of Goeddel et al., *Nature*, 290: 20-26 (1981). For cDNA encoding the amino acid sequence of IFN-α7 (IFN-αJ), see Cohen et al., *Dev. Biol. Standard*, 60: 111-122 (1985). DNAs encoding the interferons of interest can be prepared by a variety of methods known in the art. These methods include, but are not limited to, chemical synthesis by any of the methods described in Engels et al., *Agnew. Chem. Int. Ed. Engl.*, 28: 716-734 (1989), such as the triester, phosphite, phosphoramidite and H-phosphonate methods. In one embodiment, codons preferred by the expression host cell are used in the design of the interferon-encoding DNA. Alternatively, DNA encoding the interferon can be isolated from a genomic or cDNA library.

Following construction of the DNA molecule encoding the interferon of interest, the DNA molecule is operably linked to an expression control sequence in an expression vector, such as a plasmid, wherein the control sequence is recognized by a host cell transformed with the vector. In general, plasmid vectors contain replication and control sequences which are derived from species compatible with the host cell. The vector ordinarily carries a replication site, as well as sequences which encode proteins that are capable of providing phenotypic selection in transformed cells.

For expression in prokaryotic hosts, suitable vectors include pBR322 (ATCC No. 37,017), phGH107 (ATCC No. 40,011), pBO475, pS0132, pRIT5, any vector in the pRIT20 or pRIT30 series (Nilsson and Abrahmsen, *Meth. Enzymol.*, 185: 144-161 (1990)), pRIT2T, pKK233-2, pDR540 and pPL-lambda. Prokaryotic host cells containing the expression vectors suitable for use herein include *E. coli* K12 strain 294 (ATCC NO. 31446), *E. coli* strain JM101 (Messing et al., *Nucl. Acid Res.*, 9: 309 (1981)), *E. coli* strain B, *E. coli* strain χ1776 (ATCC No. 31537), *E. coli* c600 (Appleyard, *Genetics*, 39: 440 (1954)), *E. coli* W3110 (F-, gamma-, prototrophic, ATCC No. 27325), *E. coli* strain 27C7 (W3110, tonA, phoA E15, (argF-lac)169, ptr3, degP41, ompT, kan$^r$) (U.S. Pat. No. 5,288,931, ATCC No. 55,244), *Bacillus subtilis, Salmonella typhimurium, Serratia marcesans*, and *Pseudomonas* species.

In addition to prokaryotes, eukaryotic organisms, such as yeasts, or cells derived from multicellular organisms can be used as host cells. For expression in yeast host cells, such as common baker's yeast or *Saccharomyces cerevisiae*, suitable vectors include episomally replicating vectors based on the 2-micron plasmid, integration vectors, and yeast artificial chromosome (YAC) vectors. For expression in insect host cells, such as Sf9 cells, suitable vectors include baculoviral vectors. For expression in plant host cells, particularly dicotyledonous plant hosts, such as tobacco, suitable expression vectors include vectors derived from the Ti plasmid of *Agrobacterium tumefaciens*.

However, interest has been greatest in vertebrate host cells. Examples of useful mammalian host cells include monkey kidney CV1 line transformed by SV40 (COS-7, ATCC CRL 1651); human embryonic kidney line (293 or 293 cells subcloned for growth in suspension culture, Graham et al., *J. Gen Virol.,* 36: 59 (1977)); baby hamster kidney cells (BHK, ATCC CCL 10); Chinese hamster ovary cells/-DHFR (CHO, Urlaub and Chasin, *Proc. Natl. Acad. Sci. USA,* 77: 4216 (1980)); mouse sertoli cells (TM4, Mather, *Biol. Reprod.,* 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383: 44-68 (1982)); MRC 5 cells; FS4 cells; and a human hepatoma cell line (Hep G2). For expression in mammalian host cells, useful vectors include vectors derived from SV40, vectors derived from cytomegalovirus such as the pRK vectors, including pRK5 and pRK7 (Suva et al., *Science,* 237: 893-896 (1987), EP 307,247 (Mar. 15, 1989), EP 278,776 (Aug. 17, 1988)) vectors derived from vaccinia viruses or other pox viruses, and retroviral vectors such as vectors derived from Moloney's murine leukemia virus (MoMLV).

Optionally, the DNA encoding the interferon of interest is operably linked to a secretory leader sequence resulting in secretion of the expression product by the host cell into the culture medium. Examples of secretory leader sequences include stII, ecotin, lamB, herpes GD, lpp, alkaline phosphatase, invertase, and alpha factor. Also suitable for use herein is the 36 amino acid leader sequence of protein A (Abrahmsen et al., *EMBO J.,* 4: 3901 (1985)).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., *Molecular Cloning* (2nd ed.), Cold Spring Harbor Laboratory, NY (1989), is generally used for prokaryotes or other cells that contain substantial cell-wall barriers. Infection with *Agrobacterium tumefaciens* is used for transformation of certain plant cells, as described by Shaw et al., *Gene,* 23: 315 (1983) and WO 89/05859 published 29 Jun. 1989. For mammalian cells without such cell walls, the calcium phosphate precipitation method described in sections 16.30-16.37 of Sambrook et al., supra, is preferred. General aspects of mammalian cell host system transformations have been described by Axel in U.S. Pat. No. 4,399,216 issued 16 Aug. 1983. Transformations into yeast are typically carried out according to the method of Van Solingen et al., *J. Bact.,* 130: 946 (1977) and Hsiao et al., *Proc. Natl. Acad. Sci. (USA),* 76: 3829 (1979). However, other methods for introducing DNA into cells such as by nuclear injection, electroporation, or by protoplast fusion may also be used.

Prokaryotic host cells used to produce the interferon of interest can be cultured as described generally in Sambrook et al., supra.

The mammalian host cells used to produce the interferon of interest can be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham and Wallace, *Meth. Enz.,* 58: 44 (1979), Barnes and Sato, *Anal. Biochem.,* 102: 255 (1980), U.S. Pat. Nos. 4,767,704; 4,657,866; 4,927,762; or 4,560,655; WO 90/03430; WO 87/00195; U.S. Pat. Re. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

In an intracellular expression system or periplasmic space secretion system, the recombinantly expressed interferon protein can be recovered from the culture cells by disrupting the host cell membrane/cell wall (e.g. by osmotic shock or solubilizing the host cell membrane in detergent). Alternatively, in an extracellular secretion system, the recombinant protein can be recovered from the culture medium. As a first step, the culture medium or lysate is centrifuged to remove any particulate cell debris. The membrane and soluble protein fractions are then separated. Usually, the interferon is purified from the soluble protein fraction. If the IFN-α is expressed as a membrane bound species, the membrane bound peptide can be recovered from the membrane fraction by solubilization with detergents. The crude peptide extract can then be further purified by suitable procedures such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins and ligand affinity using interferon receptor immobilized on a matrix.

Many of the human IFN-α used herein can be obtained from commercial sources, e.g. from Sigma (St. Louis, Mo.), Calbiochem-Novabiochem Corporation (San Diego, Calif.) or ACCURATE Chemical & Scientific Corporation (Westbury, N.Y.).

Standard cloning procedures described in Maniatis et al., *Molecular Cloning: A Laboratory Manual*, Cold Spring Harbor Laboratory Press, Cold Spring Harbor, N.Y. (1989) are used to construct plasmids that direct the translocation of the various species of IFN-α into the periplasmic space of *E. coli*. PCR reactions are performed on cDNA clones of the various subspecies of hIFN-α disclosed in Goeddel et al., *Nature* 290: 20-26 (1981) with NsiI and StyI restriction sites added to the primers. These PCR products are then subcloned into the corresponding sites of the expression vector pB0720 described in Cunningham et al., *Science* 243:1330-1336 (1989). The resulting plasmids place production of the hIFN-α subtypes under control of the *E. coli* phoA promoter and the heat-stable enterotoxin II signal peptide as described in Chang et al., *Gene* 55: 189-196 (1987). The correct DNA sequence of each gene is confirmed using the United States Biochemical Sequenase Kit version 2.0. Each plasmid is transformed into the *E. coli* strain 27C7 (ATCC #55244) and grown in 10 liter fermentors as described in Carter et al., *Bio/Technology* 10: 163-167 (1992). Human hIFNs are purified from *E. coli* paste containing each IFN-α by affinity chromatography. Bacterial cells are lysed, and the lysate is centrifuged at 10,000×g to remove debris. The supernatant is applied to an immunoaffinity column containing a mouse anti-hIFN-αB antibody (LI-1) that is obtained as described in Staehelin et al., *Proc. Natl. Acad. Sci.* 78:1848-1852 (1981). LI-1 is immobilized on controlled pore glass by a modification of the method of Roy et al., *Journal of Chromatography*, 303: 225-228 (1984). The bound interferon is eluted from the column with 0.1 M citrate, pH 3.0, containing 20% (w/v) glycerol. The purified IFN is analyzed by SDS-PAGE and immunoblotting, and is assayed for bioactivity by the hIFN-induced anti-viral assay as described herein.

Human IFN-α2/1 hybrid molecule (IFN-α$2_{1-62}$/α$_{64-166}$) was obtained as described in Rehberg et al., *J. Biol. Chem.*, 257: 11497-11502 (1992) or Horisberger and Marco, *Pharmac. Ther.*, 66: 507-534 (1995).

b. Immobilization of IFN-α

The purified IFN-α can be attached to a suitable matrix such as agarose beads, acrylamide beads, glass beads, cellulose, various acrylic copolymers, hydroxyl methacrylate gels, polyacrylic and polymethacrylic copolymers, nylon, neutral and ionic carriers, and the like, for use in the affinity chromatographic separation of phage display clones. Attachment of the IFN-α protein to the matrix can be accomplished by the methods described in *Methods in Enzymology*, vol. 44 (1976). A commonly employed technique for attaching protein ligands to polysaccharide matrices, e.g. agarose, dextran or cellulose, involves activation of the carrier with cyanogen halides and subsequent coupling of the peptide ligand's primary aliphatic or aromatic amines to the activated matrix.

Alternatively, IFN-α can be used to coat the wells of adsorption plates, expressed on host cells affixed to adsorption plates or used in cell sorting, or conjugated to biotin for capture with streptavidin-coated beads, or used in any other art-known method for panning phage display libraries.

c. Panning Procedures

The phage library samples are contacted with immobilized IFN-α under conditions suitable for binding of at least a portion of the phage particles with the adsorbent. Normally, the conditions, including pH, ionic strength, temperature and the like are selected to mimic physiological conditions. The phage bound to the solid phase are washed and then eluted by acid, e.g. as described in Barbas et al., *Proc. Natl. Acad. Sci USA*, 88: 7978-7982 (1991), or by alkali, e.g. as described in Marks et al., *J. Mol. Biol.*, 222: 581-597 (1991), or by IFN-α antigen, e.g. in a procedure similar to the antigen competition method of Clackson et al., *Nature*, 352: 624-628 (1991). Phage can be enriched 20-1,000-fold in a single round of selection. Moreover, the enriched phage can be grown in bacterial culture and subjected to further rounds of selection.

In a preferred embodiment, phage are serially incubated with various IFN-α subtypes immobilized in order to identify and further characterize phage clones that exhibit appreciable binding to a majority, preferably all, of IFN-α subtypes. In this method, phage are first incubated with one specific IFN-α subtype. The phage bound to this subtype are eluted and subjected to selection with another IFN-α subtype. The process of binding and elution is thus repeated with all IFN-α subtypes. At the end, the procedure yields a population of phage displaying antibodies with broad reactivity against all IFN-α subtypes. These phage can then be tested against other IFN species, i.e. other than IFN-α, in order to select those clones which do not show appreciable binding to other species of IFNs. Finally, the selected phage clones can be examined for their ability to neutralize biological activity, e.g. anti-viral activity, of various IFN-α subtypes, and clones representing antibodies with broad neutralization activity against a majority, preferably all, of IFN-α subtypes are finally selected.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

It is possible to select between phage antibodies of different affinities, even with affinities that differ slightly, for IFN-α. However, random mutation of a selected antibody (e.g. as performed in some of the affinity maturation techniques described above) is likely to give rise to many mutants, most binding to antigen, and a few with higher affinity. With limiting IFN-α, rare high affinity phage could be competed out. To retain all the higher affinity mutants, phage can be incubated with excess biotinylated IFN-α, but with the biotinylated IFN-α at a concentration of lower molarity than the target molar affinity constant for IFN-α. The high affinity-binding phage can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phage with lower affinity. Conditions used in washing phage bound to a solid phase can also be manipulated to discriminate on the basis of dissociation kinetics.

In one embodiment, phage are serially incubated with various IFN-α subtypes immobilized on a solid support, such as chromatographic polymer matrix beads described above. In this method, the phage are first incubated with one specific IFN-α subtype. The phage bound to this subtype are eluted from solid phase with a suitable eluent, such as any salt or acid buffer capable of releasing the bound phage into solution. Next, the eluted phage clones are subjected to selection with another IFN-α subtype. In order to enrich the population for clones that compete with soluble IFNAR2 for binding to IFN-α, the phage clones recovered from the series of IFN-α subtype chromatographic separations are incubated with a complex of immobilized IFNAR2 preadsorbed to IFN-α, and the non-adsorbed phage clones are recovered from the incubation reaction mixture.

The selection procedures can be designed to utilize any suitable batch chromatographic technique. In one embodiment, the phage clones are adsorbed to IFN-α-derivatized polymer matrix beads in suspension, the adsorbed beads are recovered by centrifugation, the recovered beads are resuspended and incubated in a suitable elution buffer, such as any salt or acid buffer capable of releasing the bound phage into solution, the elution mixture is centrifuged, the eluted phage clones are recovered from the supernatant, and then the adsorption/elution procedure is repeated for every additional IFN-α subtype. In order to enrich the population for clones that compete with soluble IFNAR2 for binding to IFN-α, the phage clones recovered from the IFN-α subtype chromatographic separations are incubated with a suspension of IFNAR2-derivatized polymer matrix beads preadsorbed to IFN-α, the incubation mixture is centrifuged, and the non-adsorbed phage clones are recovered from the supernatant.

In another embodiment, the selection procedure is designed to enrich the phage population for the property of inhibiting IFN-α binding to IFNAR2 during each of the affinity chromatographic separations. In this method, the phage are serially incubated with each of the specific IFN-α subtypes immobilized on a solid support and then eluted from solid phase with an eluent comprising an excess of soluble IFNAR2, such as IFNAR2 ECD-IgG Fc, under conditions wherein soluble IFNAR2 is capable of displacing any phage clone that competes with IFNAR2 for binding to the immobilized IFN-α. The process of binding and elution is thus repeated with each of the specific IFN-α subtypes.

In another embodiment, the phage clones are adsorbed to IFN-α-derivatized polymer matrix beads in suspension, the adsorbed beads are recovered by centrifugation, the recovered beads are resuspended and incubated in a suitable elution buffer comprising an excess of soluble IFNAR2 (such as IFNAR2 ECD-IgG Fc) under conditions wherein the soluble IFNAR2 is capable of displacing any phage clone that competes with IFNAR2 for binding to the immobilized IFN-α and releasing the bound phage into solution, the elution mixture is centrifuged, the eluted phage clones are recovered from the supernatant, and then the adsorption/elution procedure is repeated for every additional IFN-α subtype.

At the end, the procedure yields a population of phage displaying antibodies with IFNAR2-binding inhibition activity against a broad range of IFN-α subtypes. These phage can then be tested against other IFN species (other than IFN-α species), such as IFN-β, in order to select those clones which do not show appreciable binding to other species of IFNs. Finally, the selected phage clones can be examined for their ability to neutralize biological activity, e.g. anti-viral activity, of various IFN-α subtypes, and clones representing antibodies with broad neutralization activity against a majority, preferably all, of IFN-α subtypes are finally selected.

Activity Selection of Anti-IFN-α Clones

In one embodiment, the invention provides anti-IFN-α antibodies that bind to as well as neutralize the activity of a majority, preferably all, of IFN-α subtypes, but do not significantly bind to or neutralize the activity of any other interferon species. For example, the ability of various phage clones to neutralize the anti-viral activities of various IFN-α subtypes can be tested, essentially in the same manner as described earlier for the antibodies.

4. Preparation of Soluble IFNAR2-IgG

A cDNA encoding the human immunoglobulin fusion proteins (immunoadhesins) based on the extracellular domain (ECD) of the hIFNAR2 (pRK5 hIFNAR2-IgG clone) can be generated using methods similar to those described by Haak-Frendscho et al., *Immunology* 79: 594-599 (1993) for the construction of a murine IFN-γ receptor immunoadhesin. Briefly, the plasmid $pRKCD4_2Fc_1$ is constructed as described in Example 4 of WO 89/02922 (PCT/US88/03414 published Apr. 6, 1989). The cDNA coding sequence for the first 216 residues of the mature hIFNAR2 ECD is obtained from the published sequence (Novick et al., *Cell,* 77: 391-400 [1994]). The CD4 coding sequence in the $pRKCD4_2Fc_1$ is replaced with the hIFNAR2 ECD encoding cDNA to foam the pRK5hIFNAR2-IgG clone. hIFNAR2-IgG is expressed in human embryonic kidney 293 cells by transient transfection using a calcium phosphate precipitation technique. The immunoadhesin is purified from serum-free cell culture supernatants in a single step by affinity chromatography on a protein A-sepharose column as described in Haak-Frendscho et al. (1993), supra. Bound hIFNAR2-IgG is eluted with 0.1 M citrate buffer, pH 3.0, containing 20% (w/v) glycerol. The hIFNAR2-IgG purified is over 95% pure, as judged by SDS-PAGE.

5. Diagnostic Uses of Anti-IFN-α Antibodies

The anti-IFN-α antibodies of the invention are unique research reagents in diagnostic assays for IFN-α expression. As discussed earlier, IFN-α expression is increased in certain autoimmune diseases such as IDDM, SLE, and autoimmune thyroiditis. Increased expression of various IFN-α subtypes in such disorders can be detected and quantitated using anti-IFN-α antibodies of the instant invention with broad reactivity against a majority of IFN-α subtypes. Anti-IFN-α antibodies are also useful for the affinity purification of various IFN-α subtypes from recombinant cell culture or natural sources.

Anti-IFN-α antibodies can be used for the detection of IFN-α in any one of a number of well known diagnostic assay methods. For example, a biological sample may be assayed for IFN-α by obtaining the sample from a desired source, admixing the sample with anti-IFN-α antibody to allow the antibody to form antibody/IFN-α complex with any IFN-α subtype present in the mixture, and detecting any antibody/IFN-α complex present in the mixture. The biological sample may be prepared for assay by methods known in the art which are suitable for the particular sample. The methods of admixing the sample with antibodies and the methods of detecting antibody/IFN-α complex are chosen according to the type of assay used. Such assays include competitive and sandwich assays, and steric inhibition assays. Competitive and sandwich methods employ a phase-separation step as an integral part of the method while steric inhibition assays are conducted in a single reaction mixture.

Analytical methods for IFN-α all use one or more of the following reagents: labeled IFN-α analogue, immobilized IFN-α analogue, labeled anti-IFN-α antibody, immobilized anti-IFN-α antibody and steric conjugates. The labeled reagents also are known as "tracers."

The label used is any detectable functionality that does not interfere with the binding of IFN-α and anti-IFN-α antibody. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. Nos. 3,940,475 (fluorimetry) and U.S. Pat. No. 3,645,090 (enzymes); Hunter et al., *Nature,* 144: 945 (1962); David et al., *Biochemistry,* 13: 1014-1021 (1974); Pain et al., *J. Immunol. Methods,* 40: 219-230 (1981); and Nygren, *J. Histochem. and Cytochem.,* 30: 407-412 (1982). Preferred labels herein are enzymes such as horseradish peroxidase and alkaline phosphatase.

The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in *Methods in Enzymology,* ed. J. J. Langone and H. Van Vunakis, Vol. 73 (Academic Press, New York, N.Y., 1981), pp. 147-166.

Immobilization of reagents is required for certain assay methods. Immobilization entails separating the anti-IFN-α antibody from any IFN-α that remains free in solution. This conventionally is accomplished by either insolubilizing the anti-IFN-α antibody or IFN-α analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the anti-IFN-α antibody or IFN-α analogue afterward, e.g., by immunoprecipitation.

Other assay methods, known as competitive or sandwich assays, are well established and widely used in the commercial diagnostics industry.

Competitive assays rely on the ability of a tracer IFN-α analogue to compete with the test sample IFN-α for a limited number of anti-IFN-α antibody antigen-binding sites. The anti-IFN-α antibody generally is insolubilized before or after the competition and then the tracer and IFN-α bound to the anti-IFN-α antibody are separated from the unbound tracer and IFN-α. This separation is accomplished by decanting (where the binding partner was pre-insolubilized) or by centrifuging (where the binding partner was precipitated after the competitive reaction). The amount of test sample IFN-α is inversely proportional to the amount of bound tracer as measured by the amount of marker substance. Dose-response curves with known amounts of IFN-α are prepared and compared with the test results to quantitatively determine the amount of IFN-α present in the test sample. These assays are called ELISA systems when enzymes are used as the detectable markers.

Another species of competitive assay, called a "homogeneous" assay, does not require a phase separation. Here, a conjugate of an enzyme with the IFN-α is prepared and used such that when anti-IFN-α antibody binds to the IFN-α the presence of the anti-IFN-α antibody modifies the enzyme activity. In this case, the IFN-α or its immunologically active fragments are conjugated with a bifunctional organic bridge to an enzyme such as peroxidase. Conjugates are selected for use with anti-IFN-α antibody so that binding of the anti-IFN-α antibody inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small IFN-α fragment so that antibody to hapten is substantially unable to bind the conjugate at the same time as anti-IFN-α antibody. Under this assay procedure the IFN-α present in the test sample will bind anti-IFN-α antibody, thereby allowing anti-hapten to bind the conjugate, resulting in a change in the character of the conjugate hapten, e.g., a change in fluorescence when the hapten is a fluorophore.

Sandwich assays particularly are useful for the determination of IFN-α or anti-IFN-α antibodies. In sequential sandwich assays an immobilized anti-IFN-α antibody is used to adsorb test sample IFN-α, the test sample is removed as by washing, the bound IFN-α is used to adsorb a second, labeled anti-IFN-α antibody and bound material is then separated from residual tracer. The amount of bound tracer is directly proportional to test sample IFN-α. In "simultaneous" sandwich assays the test sample is not separated before adding the labeled anti-IFN-α. A sequential sandwich assay using an anti-IFN-α monoclonal antibody as one antibody and a polyclonal anti-IFN-α antibody as the other is useful in testing samples for IFN-α.

The foregoing are merely exemplary diagnostic assays for IFN-α. Other methods now or hereafter developed that use anti-IFN-α antibody for the determination of IFN-α are included within the scope hereof, including the bioassays described above.

6. Therapeutic Compositions and Administration of Anti-IFN-α Antibodies

Therapeutic formulations of the anti-IFN-α antibodies of the invention are prepared for storage by mixing antibody having the desired degree of purity with optional physiologically acceptable carriers, excipients, or stabilizers (*Remington: The Science and Practice of Pharmacy,* 19th Edition, Alfonso, R., ed, Mack Publishing Co. (Easton, Pa.: 1995)), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The anti-IFN-α antibody to be used for in vivo administration must be sterile. This is readily accomplished by filtration through sterile filtration membranes, prior to or following lyophilization and reconstitution. The anti-IFN-α antibody ordinarily will be stored in lyophilized form or in solution.

Therapeutic anti-IFN-α antibody compositions generally are placed into a container having a sterile access port, for example, an intravenous solution bag or vial having a stopper pierceable by a hypodermic injection needle.

The route of anti-IFN-α antibody administration is in accord with known methods, e.g. injection or infusion by intravenous, intraperitoneal, intracerebral, subcutaneous, intramuscular, intraocular, intraarterial, intracerebrospinal, or intralesional routes, or by sustained release systems as noted below. Preferably the antibody is given systemically.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al., *Biopolymers,* 22: 547-556 (1983)), poly(2-hydroxyethyl-methacrylate) (Langer et al., *J. Biomed. Mater. Res.,* 15: 167-277 (1981) and Langer, *Chem. Tech.,* 12: 98-105 (1982)), ethylene vinyl acetate (Langer et al., supra) or poly-D-(−)-3-hydroxybutyric acid (EP 133,988). Sustained-release anti-IFNAR2 antibody compositions also include liposomally entrapped antibody. Liposomes containing antibody are prepared by methods known per se: DE 3,218,121; Epstein et al., *Proc. Natl. Acad. Sci. USA,* 82: 3688-3692 (1985); Hwang et al., *Proc. Natl. Acad. Sci. USA,* 77: 4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamelar type in which the lipid content is greater than about 30 mol. % cholesterol, the selected proportion being adjusted for the optimal antibody therapy.

Anti-IFN-α antibody can also be administered by inhalation. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-IFN-α antibody can be aerosolized using a fluorocarbon formulation and a metered dose inhaler, or inhaled as a lyophilized and milled powder.

An "effective amount" of anti-IFN-α antibody to be employed therapeutically will depend, for example, upon the therapeutic objectives, the route of administration, the type of anti-IFN-α antibody employed, and the condition of the patient. Accordingly, it will be necessary for the therapist to titer the dosage and modify the route of administration as required to obtain the optimal therapeutic effect. Typically, the clinician will administer the anti-IFN-α antibody until a dosage is reached that achieves the desired effect. The progress of this therapy is easily monitored by conventional assays.

The patients to be treated with the anti-IFN-α antibody of the invention include preclinical patients or those with recent onset of immune-mediated disorders, and particularly autoimmune disorders. Patients are candidates for therapy in accord with this invention until such point as no healthy tissue remains to be protected from immune-mediated destruction. For example, a patient suffering from insulin-dependent diabetes mellitus (IDDM) can benefit from therapy with an anti-IFN-α antibody of the invention until the patient's pancreatic islet cells are no longer viable. It is desirable to administer an anti-IFN-α antibody as early as possible in the development of the immune-mediated or autoimmune disorder, and to continue treatment for as long as is necessary for the protection of healthy tissue from destruction by the patient's immune system. For example, the IDDM patient is treated until insulin monitoring demonstrates adequate islet response and other indicia of islet necrosis diminish (e.g. reduction in anti-islet antibody titers), after which the patient can be withdrawn from anti-IFN-α antibody treatment for a trial period during which insulin response and the level of anti-islet antibodies are monitored for relapse.

In the treatment and prevention of an immune-mediated or autoimmune disorder by an anti-IFN-α antibody, the antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the antibody, the particular type of antibody, the method of administration, the scheduling of administration, and other factors known to medical practitioners. The "therapeutically effective amount" of antibody to be administered will be governed by such considerations, and is the minimum amount necessary to prevent, ameliorate, or treat the disorder, including treating chronic autoimmune conditions and immunosuppression maintenance in transplant recipients. Such amount is preferably below the amount that is toxic to the host or renders the host significantly more susceptible to infections.

As a general proposition, the initial pharmaceutically effective amount of the antibody administered parenterally will be in the range of about 0.1 to 50 mg/kg of patient body weight per day, with the typical initial range of antibody used being 0.3 to 20 mg/kg/day, more preferably 0.3 to 15 mg/kg/day. The desired dosage can be delivered by a single bolus administration, by multiple bolus administrations, or by continuous infusion administration of antibody, depending on the pattern of pharmacokinetic decay that the practitioner wishes to achieve.

As noted above, however, these suggested amounts of antibody are subject to a great deal of therapeutic discretion. The key factor in selecting an appropriate dose and scheduling is the result obtained, as indicated above.

The antibody need not be, but is optionally formulated with one or more agents currently used to prevent or treat the immune-mediated or autoimmune disorder in question. For example, in rheumatoid arthritis, the antibody may be given in conjunction with a glucocorticosteroid. The effective amount of such other agents depends on the amount of anti-IFN-α antibody present in the formulation, the type of disorder or treatment, and other factors discussed above. These are generally used in the same dosages and with administration routes as used hereinbefore or about from 1 to 99% of the heretofore employed dosages.

Further details of the invention can be found in the following example, which further defines the scope of the invention. All references cited throughout the specification, and the references cited therein, are hereby expressly incorporated by reference in their entirety.

EXAMPLES

The following examples are offered by way of illustration and not by way of limitation. The examples are provided so as to provide those of ordinary skill in the art with a complete disclosure and description of how to make and use the compounds, compositions, and methods of the invention and are not intended to limit the scope of what the inventors regard as their invention. Efforts have been made to insure accuracy with respect to numbers used (e.g. amounts, temperature, etc.) but some experimental errors and deviation should be accounted for. Unless indicated otherwise, parts are parts by weight, temperature is in degrees C., and pressure is at or near atmospheric. The disclosures of all citations in the specification are expressly incorporated herein by reference.

Example 1

Generation and Characterization of a Broad Reactive Mouse Anti-IFN-α Monoclonal Antibody Materials and Methods
A Murine Monoclonal Antibody with Broad Reactivity Against IFN-α Subtypes A pan-IFN-α neutralizing antibody was developed by sequentially immunizing mice with the mixture of human IFN-α subtypes, generating a large number of candidate mAbs, and then screening for binding and activity. In particular, Balb/c mice were immunized into each hind footpad 9 times (at two week intervals) with 2.5 µg of lymphoblastoid hIFN-α (Product No. 1-9887 of Sigma, St. Louis, Mo.) resuspended in MPL-TDM (Ribi Immunochemical Research, Inc., Hamilton, Mont.). Three days after the final boost, popliteal lymph node cells were fused with murine myeloma cells P3X63Ag8.U.1 (ATCC CRL1597), using 35% polyethylene glycol. Hybridomas were selected in HAT medium. Ten days after the fusion, hybridoma culture supernatants were first screened for mAbs binding to the various species of hIFN-α in an ELISA. The selected hybridoma culture supernatants were then tested for their ability to inhibit the anti-viral cytopathic effect of IFN on human lung carcinoma cell line A549 cells as described below. As indicated in FIG. 1, three mAbs obtained from 1794 fusion wells were able to neutralize a diverse set of IFN-α subtypes. These three mAbs were subcloned and re-analyzed.

Neutralization of Antiviral Activity of IFN-α

The ability of a candidate antibody to neutralize the antiviral activity of IFN-α was assayed as described by Yousefi, S., et al., *Am. J. Clin. Pathol.*, 83: 735-740 (1985). Briefly, the assay was performed using human lung carcinoma A549 cells challenged with encephalomyocarditis (EMC) virus. Serial dilutions of mAbs were incubated with various units of type I interferons for one hour at 37° C. in a total volume of 100 µl. These mixtures were then incubated with $5 \times 10^5$ A549 cells in 100 µl of cell culture medium for 24 hours. Cells were then challenged with $2 \times 10^5$ pfu of EMC virus for an additional 24 hours. At the end of the incubation, cell viability was determined by visual microscopic examination or crystal violet staining. The neutralizing antibody titer (EC50) was defined as the concentration of antibody which neutralizes 50% of the anti-viral cytopathic effect by 100 units/ml of type I IFNs. The units of type I IFNs used in this study were determined using NIH reference recombinant human IFN-α2 as a standard. The specific activities of the various type I IFNs tested were as follows: IFN-α2/-α1 (IFN-α2 residues 1-62/-α1 residues 64-166) ($2 \times 10^7$ IU/mg), IFN-α1 ($3 \times 10^7$ IU/mg), IFN-α2 ($2 \times 10^7$ IU/mg), IFN-α5 ($8 \times 10^7$ IU/mg), IFN-α8 ($19 \times 10^7$ IU/mg), and IFN-α10 ($1.5 \times 10^5$ IU/mg). The leukocyte IFN tested was Sigma Product No. 1-2396. The lymphoblastoid IFN tested was NIH reference standard Ga23-901-532. The data shown in FIG. 3B was obtained using the above-described assay format in experiments performed by Access Biomedical (San Diego, Calif.) at the behest of applicant.

Electrophoretic Mobility Shift Assay

Most of the immediate actions of IFN have been linked to activation of latent cytoplasmic signal transducers and activators of transcription (STAT) proteins to produce a multiprotein complex, interferon-stimulated gene factor-3 (ISGF3), which induces transcription from target promoter interferon-stimulated response element (ISRE). ISGF3 is composed of three protein subunits: STAT1, STAT2 and p48/ISGF3γ. The p48 protein belongs to the interferon regulatory factor (IRF) family, and is a DNA-binding protein that directly interacts with ISRE. Thus, monitoring ISRE specific cellular DNA-binding complex in response to IFN treatment provides a simple, rapid and convenient method to assess the effect of IFN on target cells. One of the convenient formats to carry out such an analysis is electrophoretic mobility shift assay (EMSA), wherein the induction of an ISRE-binding activity by IFN treatment results in the shift in the electrophoretic mobility of a radiolabeled double-stranded oligonucleotide probe corresponding to the consensus sequence of ISRE.

The assay was carried out essentially as described by Kurabayashi et al., *Mol. Cell Biol.*, 15: 6386 (1995). Briefly, 5 ng of a specific IFN-α subtype plus various concentrations (5-100 µg/ml) of anti-IFN-α mAbs were incubated with $5 \times 10^5$ HeLa cells in 200 µl of DMEM for 30 minutes at 37° C. Cells were preincubated with antibody for 15 minutes at 4° C. before the addition of the hIFN-α. Cells were washed in PBS and resuspended in 125 µl buffer A (10 mM HEPES, pH 7.9, 10 mM KCl, 0.1 mM ETDA, 1 mM DTT, 1 mM phenylmethylsulfonyl fluoride, 10 µg/ml leupeptin, 10 µg/ml aprotinin). After a 15 minute incubation on ice, cells were lysed by the addition of 0.025% NP40. The nuclear pellet was obtained by centrifugation and was resuspended in 50 µl buffer B (20 mM HEPES, pH 7.9, 400 mM NaCl, 0.1 mM EDTA, 1 mM DTT, 1 mM phenylmethylsulfonyl fluoride, 10 µg/ml leupeptin, 10 µg/ml aprotinin) and kept on ice for 30 min. The nuclear fraction was cleared by centrifugation and the supernatant stored at −70° C. until use. Double-stranded probes were prepared from single-stranded oligonucleotides (ISG15 top: 5'-GATCGGGAAAGGGAAACCGAAACTGAAGCC-3' [SEQ ID NO. 13], ISG15 bottom: 5'-GATCGGCT-TCAGTTTCGGTTTCCCTTTC CC-3' [SEQ ID NO. 14]) utilizing a DNA polymerase I Klenow filling reaction with $^{32}$P-dATP (3,000 Ci/mM, Amersham). Labeled oligonucleotides were purified from unincorporated radioactive nucleotides using BIO-Spin 30 columns (Bio-Rad). Binding reactions containing 5 µl nuclear extract, 25,000 cpm of labeled probe and 2 µg of non-specific competitor poly (dI-dC)-poly (dI-dC) in 15 µl binding buffer (10 mM Tris-HCL, pH 7.5, 50 mM NaCl, 1 mM EDTA, 1 mM DTT, 1 mM phenylmethylsulfonyl fluoride and 15% glycerol) were incubated at RT for 30 minutes. DNA-protein complexes were resolved in 6% non-denaturing polyacrylamide gels and analyzed by autoradiograph. The specificity of the assay was determined by the addition of 350 ng of unlabeled ISG15 probe in separate reaction mixtures. Formation of an ISGF3 specific complex was confirmed by a super shift assay with anti-STAT1 antibody.

Cloning of a Gene Encoding 9F3 Anti-IFN-α Monoclonal Antibody

The murine anti-human IFN-α mAb 9F3 was generated, cloned and sequenced. The plasmid pEMX1 used for expression and mutagenesis of F(ab)s in *E. coli* has been described previously (Werther et al., *J. Immunol.* 157: 4986-4995 [1996]). Briefly, the plasmid contains a DNA fragment encoding a consensus human κ subgroup 1 light chain (VLκ1-CL) and a consensus human subgroup III heavy chain (VHIII-CH1) and an alkaline phosphatase promoter. The use of the consensus sequences for VL and VH has been described previously (Carter et al., *Proc. Natl. Acad. Sci. USA* 89: 4285-4289 [1992]).

Results

We have previously shown that there is a wide spectrum of IFN-α subtypes expressed by the islets of patients with IDDM (Huang et al., *Diabetes* 44: 658-664 [1995]). We also demonstrated that there is no obvious association between IDDM and the expression of either IFN-β or IFN-γ (Huang et al., [1995] supra). While the specific IFN-α subtypes expressed as part of the SLE pathology have not been defined, as with IDDM, the association is with IFN-α and not with either of IFN-β or IFN-γ (Hooks, et al., *Arthritis & Rheumatism* 25: 396-400 [1982]; Kim, et al., *Clin. Exp. Immunol.* 70: 562-569 [1987]; Lacki, et al., *J. Med.* 28: 99-107 [1997]; Robak, et al., *Archivum Immunologiae et Therapiae Experimentalis* 46: 375-380 [1998]; Shiozawa, et al., *Arthritis & Rheumatism* 35: 417-422 [1992]; von Wussow, et al., *Rheumatology International* 8: 225-230 [1988]). These observations led us to propose that a candidate antibody for therapeutic intervention in IDDM or SLE would need to neutralize a majority of the IFN-α subtypes while leaving intact the activities of other interferons (β, γ, and ω) and interleukins that may be required for host defense.

Figure 2:
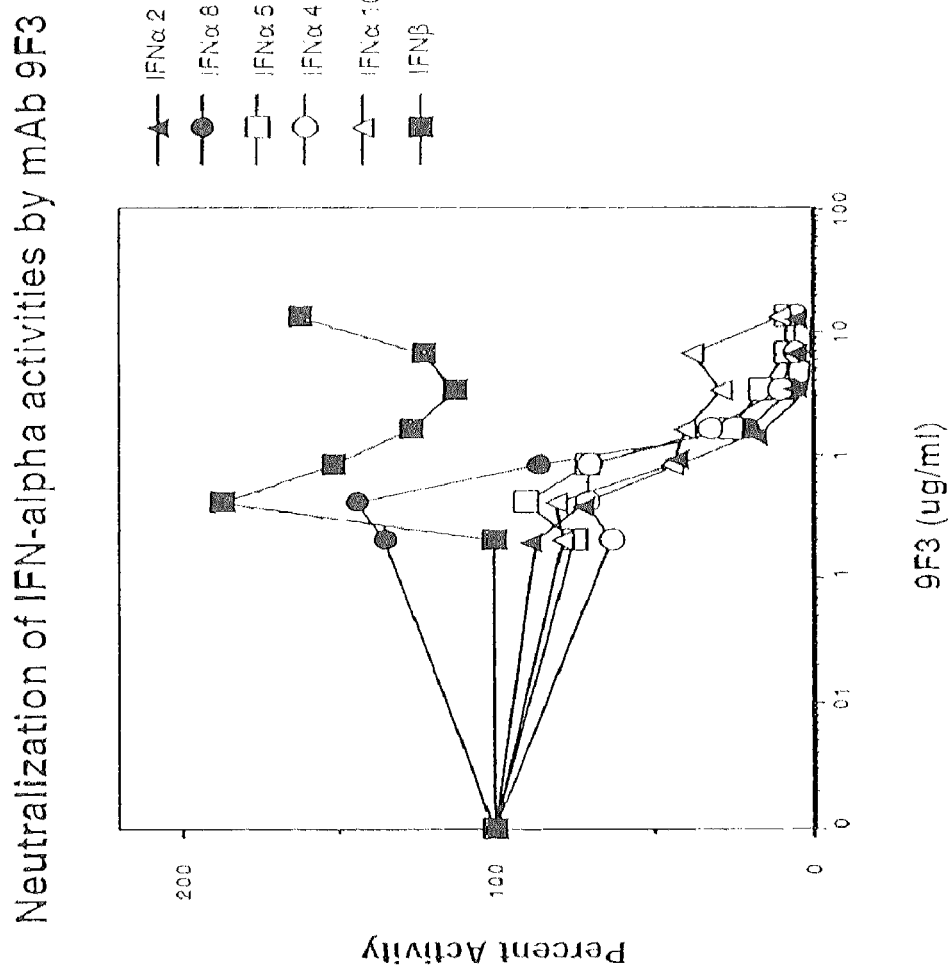
FIG. 2 shows that a murine anti-human IFN-α mAb (9F3) is able to neutralize a spectrum of recombinant IFN-α subtypes but not recombinant IFN-β. The indicated IFN's were assayed for inhibition of encephalomyocarditis (EMC) viral growth in A549 cells in the presence of increasing concentrations of the mAb 9F3. Data are presented as the percentage of the viral growth inhibition activity obtained with the indicated IFN in the absence of mAb 9F3.
Figure 3:
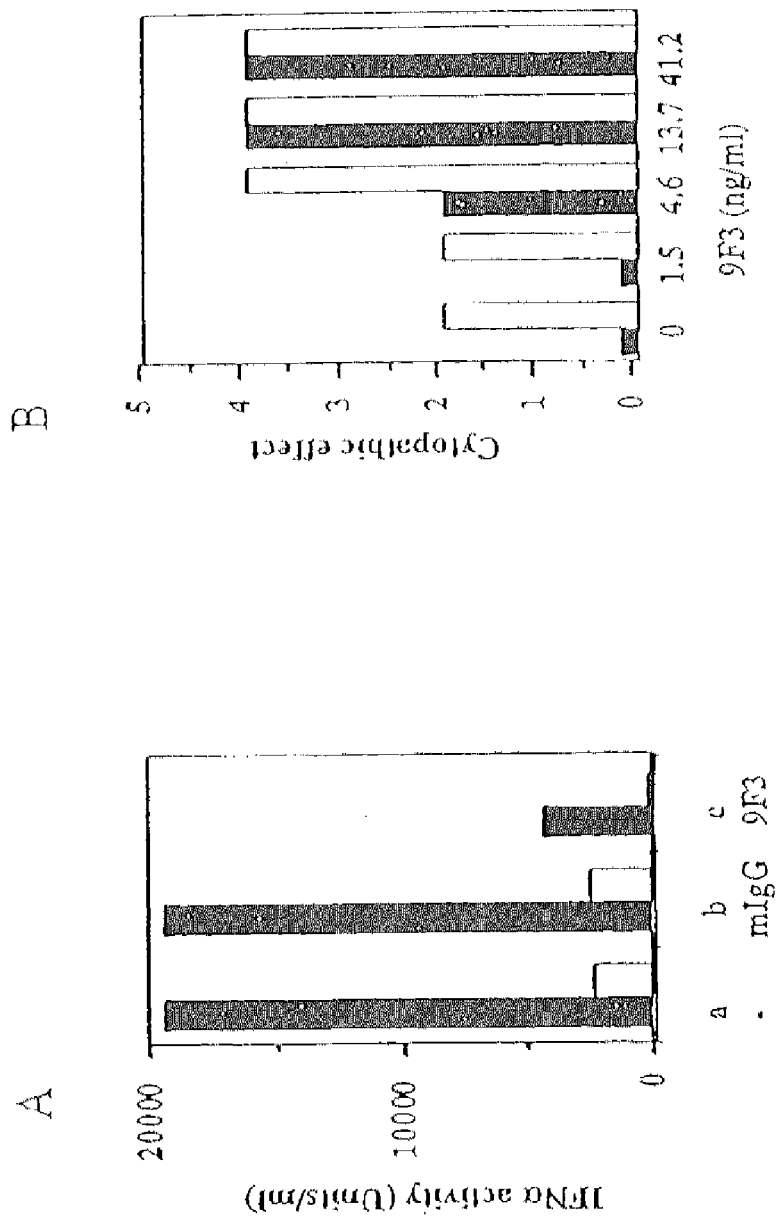
FIGS. 3A-3B show the neutralization of leukocyte interferon (Sigma) (FIG. 3A) and lymphoblastoid interferon (NIH reference Ga23-901-532) (FIG. 3B).

One of them (9F3) was able to neutralize a wide spectrum of recombinant interferon α subtypes and was further characterized. As shown in FIG. 2A, 9F3 was able to neutralize the anti-viral activity of seven recombinant interferons, IFN-α-2, 4, 5, 8 and 10 (FIG. 2) and IFN-α1 and 21 (Table 2 and FIG. 6). These IFN-α subtypes cover the full spectrum of sequences as projected in a type I interferon sequence dendrogram. More importantly, the 9F3 mAb that neutralized the IFN-α subtypes was unable to neutralize IFN-β (FIG. 2, Table 2) or IFN-γ. The small increase in activity shown in FIG. 2 for IFN-β was not reproducible in other assays and appears to be the result of assay variation.

Other mAbs that are neutralizing toward IFN-α have been developed (Tsukui et al., *Microbiol. Immunol.* 30: 1129-1139 [1986]; Berg, *J. Interferon Res.* 4: 481-491 [1984]; Meager and Berg, *J. Interferon Res.* 6:729-736 [1986]; U.S. Pat. No. 4,902,618; and EP publication No. 0,139,676 B1). However, these antibodies neutralize only a limited number of recombinant IFN-α subtypes and are unable to neutralize a wide spectrum of IFN-α subtypes such as those produced by activated leukocytes. In contrast, 9F3 Mab was able to neutralize at least 95% of the anti-viral activity in the heterogeneous collection of IFN-α subtypes produced by activated leukocytes (FIG. 3A). Similarly, 9F3 mAb was also able to block the anti-viral activity of an independent preparation of lymphoblastoid IFN (NIH reference standard) as determined in an independent experiment (FIG. 3B).

Figure 4:
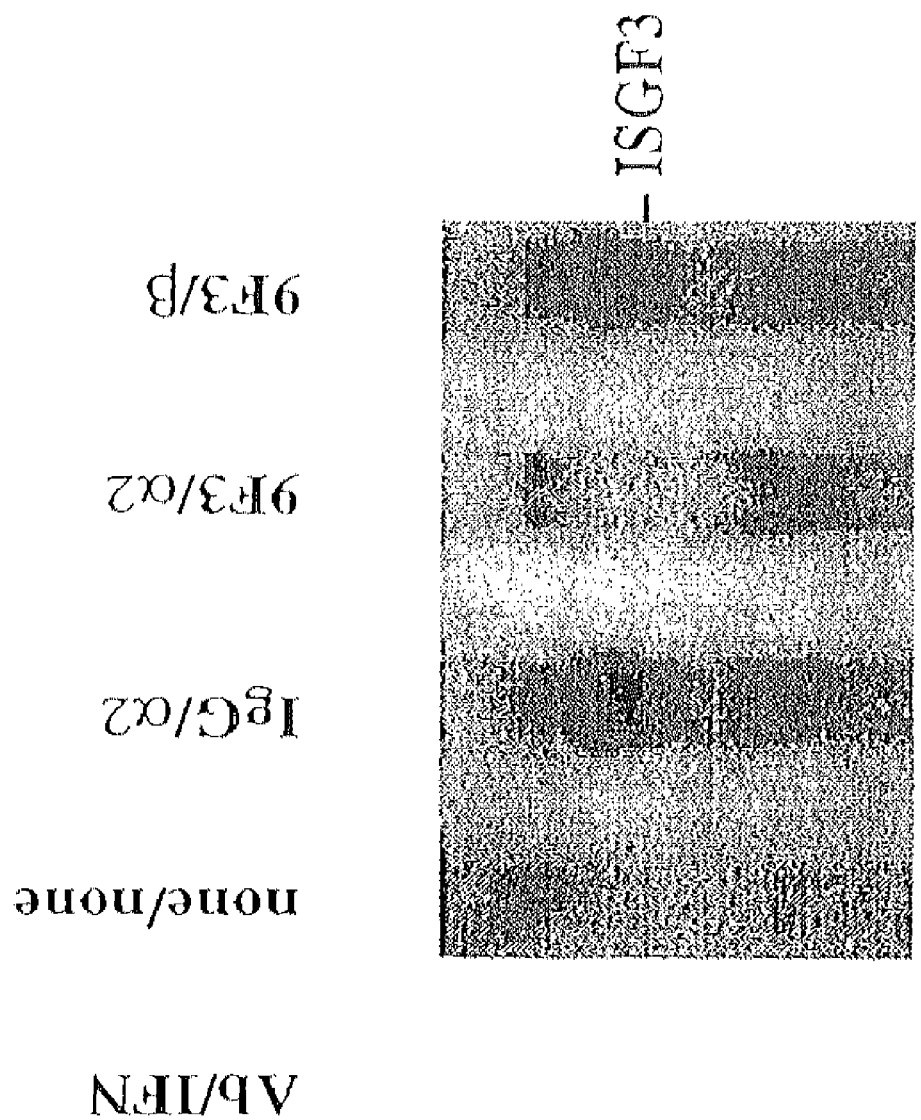
FIG. 4 depicts results of an electrophoretic mobility shift assay (EMSA) showing the induction of an ISGF3/ISRE complex by IFN-α and the ability of 9F3 mAb to prevent the formation of the complex. EMSA was performed in the presence or absence of either human IFN-α2 (denoted as "α2") or IFN-β (denoted as "β") at a concentration of 25 ng/ml with 9F3 mAb (denoted as "9F3") or murine IgG control antibody (denoted as "IgG") at a concentration of 10 μg/ml.

The ability of 9F3 mAb to neutralize IFN-α was also tested using an alternative bioassay. The assay was based on the ability of IFN-α to activate the binding of the signaling molecule, interferon-stimulated gene factor 3 (ISGF3), to an oligonucleotide derived from the interferon-stimulated response element (ISRE) in a DNA binding assay known as electrophoretic mobility shift assay (Horvath et al., *Genes Dev.* 9: 984-994 [1995]). The transduction of type I interferon signals to the nucleus relies on activation of a protein complex, ISGF3, involving two signal transducers and activators of transcription (STAT) proteins, STAT1 and STAT2, and the interferon regulatory factor (IRF) protein, p48/ISGF3γ (Wathelet et al., *Mol. Cell* 1: 507-518 [1998]). The latter is a DNA sequence recognition subunit of ISGF3 and directly interacts with ISRE (McKendry et al., *Proc. Natl. Acad. Sci. USA* 88: 11455-11459 [1991]; John et al., *Mol. Cell. Biol.* 11: 4189-4195 [1991]). The treatment of COS cells with either IFN-α or IFN-β led to the appearance of a complex corresponding to the binding of ISGF3 to the ISRE derived probe. The appearance of the IFN-α-induced but not the IFN-β-induced complex was blocked by 9F3 mAb (FIG. 4). Furthermore, 9F3 mAb was able to neutralize the activity of six recombinant IFN-α subtypes that were tested in this assay (Table 2).

Having established that 9F3 was able to neutralize both a wide variety of recombinant IFN-α subtypes and the mixture of IFN-α subtypes produced by activated leukocytes, we cloned and sequenced the cDNAs encoding both the heavy and light chains of 9F3 mAb. The heavy and light chains were purified and the N terminal amino acid sequences derived were used to design degenerate 5' primers corresponding to the N terminus, and the 3' primers were designed corresponding to the constant domain of mouse κ light chain and IgG2 heavy chain. The corresponding cDNAs were cloned using conventional PCR technique and the nucleotide sequence of the inserts was determined. FIG. 5 shows sequence alignment of VL (5A) and VH (5B) domains of a murine 9F3 monoclonal antibody, a humanized version (V13) and consensus sequence of the human heavy chain subgroup III and the human κ light chain subgroup III. In order to ensure that the cDNAs that were cloned encoded the correct Mab reflecting the specificity and characteristics of 9F3 mAb, recombinant chimeric proteins were generated that utilized the mouse cDNA sequences shown in FIG. 5 and a human all domain. The resultant chimera (CH8-2) was able to fully neutralize various recombinant IFN-α subtypes (FIG. 6). The amino acid sequences for the heavy and light chains were then used to generate a humanized antibody.

Example 2

Humanization of 9F3 Pan-IFN-α Neutralizing Monoclonal Antibody

Materials and Methods
Construction of Humanized F(ab)s

To construct the first F(ab) variant of humanized 9F3, site-directed mutagenesis (Kunkel, *Proc. Natl. Acad. Sci. USA* 82: 488-492 [1985]) was performed on a deoxyuridine-containing template of pEMX1. The six CDRs were changed to the murine 9F3 sequence (FIG. 5); the residues included in each CDR were from the sequence-based CDR definitions (Kabat et al., (1991) supra). F-1 therefore consisted of a complete human framework (VL κ subgroup 1 and VH subgroup III) with the six complete murine CDR sequences. Plasmids for all other F(ab) variants were constructed from the plasmid template of F-1. Plasmids were transformed into *E. coli* strain XL-1 Blue (Stratagene, San Diego, Calif.) for preparation of double- and single-stranded DNA using commercial kits (Qiagen, Valencia, Calif.). For each variant, DNA coding for light and heavy chains was completely sequenced using the dideoxynucleotide chain termination method (Sequenase, U.S. Biochemical Corp., Cleveland, Ohio). Plasmids were transformed into *E. coli* strain 16C9, a derivative of MM294, plated onto Luria broth plates containing 50 μg/ml carbenicillin, and a single colony selected for protein expression. The single colony was grown in 5 ml Luria broth-100 μg/ml carbenicillin for 5-8 h at 37° C. The 5 ml culture was added to 500 ml AP5 medium containing 50 μg/ml carbenicillin and allowed to grow for 20 h in a 4 L baffled shake flask

TABLE 2

Inhibition of ISGF3 formation induced by type I IFNs by mAb 9F3

| mAb | IFN-α2/1 | IFN-α1 | IFN-α2 | IFN-α5 | IFN-α8 | IFN-α21 | IFN-β |
|---|---|---|---|---|---|---|---|
| 9F3.18.5 | +++ | +++ | +++ | + | +++ | +++ | − |
| IgG1 | − | − | − | − | − | − | − |

The extent of inhibition of the IFN induced complex by 9F3 is indicated where − indicates that the induced band was not altered; + indicates that the band was partially lost and +++ indicates that the induced band was largely abolished. mAb was used at 10 μg/ml; IFN-α was used at 25 ng/ml at 30° C. AP5 medium consists of: 1.5 g glucose, 11.0 g Hycase SF, 0.6 g yeast extract (certified), 0.19 g MgSO$_4$ (anhydrous), 1.07 g NH$_4$Cl, 3.73 g KCl, 1.2 g NaCl, 120 ml 1 M triethanolamine, pH 7.4, to 1 L water and then sterile filtered through 0.1 µm Sealkeen filter. Cells were harvested by centrifugation in a 1 L centrifuge bottle at 3000×g and the supernatant removed. After freezing for 1 h, the pellet was resuspended in 25 ml cold 10 mM Tris-1 mM EDTA-20% sucrose, pH 7.5, 250 µl of 0.1 M benzamidine (Sigma, St. Louis, Mo.) was added to inhibit proteolysis. After gentle stirring on ice for 3 h, the sample was centrifuged at 40,000×g for 15 min. The supernatant was then applied to a Protein G-Sepharose CL-4B (Pharmacia, Uppsala, Sweden) column (0.5 ml bed volume) equilibrated with 10 mM Tris-1 mM EDTA, pH 7.5. The column was washed with 10 ml of 10 mM Tris-1 mM EDTA, pH 7.5, and eluted with 3 ml 0.3 M glycine, pH 3.0, into 1.25 ml 1 M Tris, pH 8.0. The F(ab) was then buffer exchanged into PBS using a Centricon-30 (Amicon, Beverly, Mass.) and concentrated to a final volume of 0.5 ml. SDS-PAGE gels of all F(ab)s were run to ascertain purity and the molecular weight of each variant was verified by electrospray mass spectrometry. F(ab) concentrations were determined using quantitative amino acid analysis.

Construction of Chimeric and Humanized IgG

For generation of human IgG2 versions of chimeric and humanized 9F3, the appropriate murine or humanized VL and VH (F-13, Table 3) domains were subcloned into separate previously described pRK vectors (Eaton et al., *Biochemistry* 25: 8343-8347 [1986]) that contained DNA coding for human IgG2 CH1-Fc or human light chain CL domain. The DNA coding for the entire light and the entire heavy chain of each variant was verified by dideoxynucleotide sequencing. The chimeric IgG consists of the entire murine 9F3 VH domain fused to a human CH1 domain at amino acid SerH113 and the entire murine 9F3 VL domain fused to a human CL domain at amino acid LysL 107.

Heavy and light chain plasmids were co-transfected into an adenovirus-transformed human embryonic kidney cell line, 293 (Graham et al., *J. Gen. Virol.* 36: 59-74 [1977]), using a high efficiency procedure (Gorman et al., *DNA Prot. Eng. Tech.* 2: 3-10 [1990]). Media was changed to serum-free and harvested daily for up to five days. Antibodies were purified from the pooled supernatants using Protein A-Sepharose CL-4B (Pharmacia). The eluted antibody was buffer exchanged into PBS using a Centricon-30 (Amicon), concentrated to 0.5 ml, sterile filtered using a Millex-GV (Millipore, Bedford, Mass.) and stored at 4° C. IgG2 concentrations were determined using quantitative amino acid analysis.

IFN-α Binding Assay

In the ELISA, 96 well microtiter plates (Nunc) were coated by adding 50 µl of 0.1 µg/ml IFN-α in PBS to each well and incubated at 4° C. overnight. The plates were then washed three times with wash buffer (PBS plus 0.05% Tween 20). The wells in microtiter plates were then blocked with 200 µl of SuperBlock (Pierce) and incubated at room temperature for 1 hour. The plates were then washed again three times with wash buffer. After washing step, 100 µl of serial dilutions of humanized mAb starting at 10 µg/ml were added to designated wells. The plates were incubated at room temperature for 1 hour on a shaker apparatus and then washed three times with wash buffer. Next, 100 µl of horseradish peroxidase (HRP)-conjugated goat anti-human Fab specific (Cappel), diluted at 1:1000 in assay buffer (0.5% bovine serum albumin, 0.05% Tween 20 in PBS), was added to each well. The plates were incubated at room temperature on a shaker apparatus and then washed three times with wash buffer, followed by addition of 100 µl of substrate (TMB, 3,3',5,5'-tetramethylbenzidine; Kirkegaard & Perry) to each well and incubated at room temperature for 10 minutes. The reaction was stopped by adding 100 µl of stop solution (from Kirkegaard & Perry) to each well, and absorbance at 450 nm was read in an automated microtiter plate reader.

BIAcore™ Biosensor Assay

IFN-α binding of the humanized F(ab)s, chimeric and humanized IgG2 antibodies were measured using a BIACore™ biosensor (Karlsson et al., *Methods: A companion to Methods in Enzymology* 6: 97-108 [1994]). The IFN-α was immobilized on the sensor chip at 60 µg/ml in 50 mM MES buffer, pH 6.3. Antibodies were exposed to the chip at 75 µg/ml (500 nM) in phosphate-buffered saline/1% Tween-20. The antibody on-rate ($k_{on}$) was measured.

Computer Graphics Modes of Murine and Humanized F(ab)s

Figure 7:
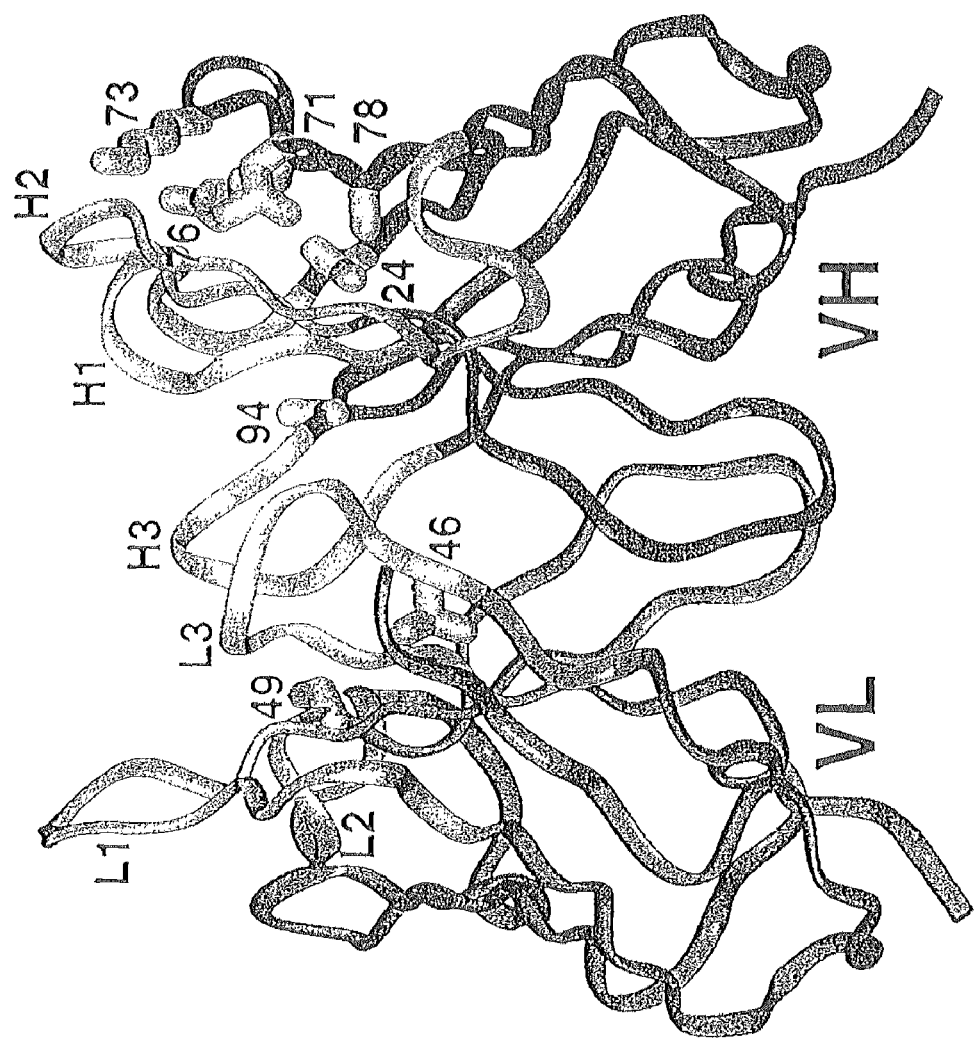
FIG. 7 depicts a model of humanized 9F3 version 13. Backbone of VL and VH domains is shown as a ribbon. CDRs are shown in white and are labeled (L1, L2, L3, H1, H2, H3). Framework side chains altered from human to murine are shown in white and are labeled by residue number.

Sequences of the VL and VH domains (FIGS. 5A and B) were used to construct a computer graphics model of the murine 9F3 VL-VH domains (FIG. 7). This model was used to determine which framework residues should be incorporated into the humanized antibody. A model of the humanized F(ab) was also constructed to verify correct selection of murine framework residues. Construction of models was performed as described previously (Carter et al., [1992] supra; Werther et al., [1996] supra).

Results

The consensus sequence for the human heavy chain subgroup III and the light chain subgroup I were used as the framework for the humanization as shown in FIG. 5 (Kabat et al., (1991), supra). This framework has been successfully used in the humanization of other murine antibodies (Carter et al., *Proc. Natl. Acad. Sci. USA* 89: 4285-4289 [1992]; Presta et al., *J. Immunol.* 151: 2623-2632 [1993]; Eigenbrot et al., *Proteins* 18: 49-62 [1994]; Werther et al., *J. Immunol.* 157: 4986-4995 [1996]). All humanized variants were initially made and screened for binding as F(ab)s expressed in *E. coli*. Typical yields from 500 ml shake flasks were 0.1-0.4 mg F(ab).

The complementarity determining region (CDR) residues have been defined either based on sequence hypervariability (Kabat et al., (1991) supra) or crystal structure of F(ab)-antigen complexes (Chothia et al., *Nature* 342: 877-883 [1989]). Although the sequence-based CDRs are larger than the structure-based CDRs, the two definitions are generally in agreement except for CDR-H1. According to the sequence-based definition, CDR-H1 includes residues H31-H35, whereas the structure-based system defines residues H26-H32 as CDR-H1 (light chain residue numbers are prefixed with L; heavy chain residue numbers are prefixed with H). For the present study, CDR-H1 was defined as a combination of the two, i.e. including residues H26-H35. The other CDRs were defined using the sequence-based definition (Kabat et al., (1991) supra).

In the initial variant, F-1, the CDR residues were transferred from the murine antibody to the human framework. In addition, F(ab)s which consisted of the chimeric heavy chain with F-1 light chain (Ch-1) and F-1 heavy chain with chimeric light chain (Ch-2) were generated and tested for binding. F-1 bound IFN-α poorly (Table 3). Comparing the binding affinities of Ch-1 and Ch-2 (Table 3) suggested that framework residues in the F-1 VH domain needed to be altered in order to increase binding.

TABLE 3

Humanized Anti-IFN-α Versions

| Version | Template | Changes[a] | OD$_{450nm}$ at 10 µg/ml Mean | SD | N |
|---|---|---|---|---|---|
| Ch-1 | F-1 VL/Murine VH | | 1.45 | 0.11 | 3 |
| Ch-2 | Murine VL/F-2 VH | | .024 | 0.04 | 3 |
| F-1 | Human FR/CDR swap | | 0.06 | 0.00 | 3 |
| F-2 | F-1 | ArgH71Leu; AsnH73Lys | 0.08 | 0.01 | 3 |
| F-3 | F-2 | PheH67Ala; IleH69Leu; LeuH78Ala | 0.14 | 0.02 | 3 |
| F-4 | F-3 | ArgH94Ser | 0.495 | 0.02 | 3 |
| F-5 | F-4 | AlaH24Thr | 0.545 | 0.03 | 3 |
| F-6 | F-5 | ValH48Ile; AlaH49Gly | 0.527 | 0.02 | 2 |
| F-7 | F-5 | *Ala*H78*Leu* | 0.259 | 0.02 | 2 |
| F-8 | F-5 | *Leu**H69Ile* | 0.523 | 0.05 | 3 |
| F-9 | F-5 | *Ala*H67*Phe* | 0.675 | 0.09 | 3 |
| F-10 | F-9 | *Leu**H69Ile* | 0.690 | 0.03 | 3 |
| F-11 | F-10 | LysH75Ser | 0.642 | 0.06 | 3 |
| F-12 | F-10 | AsnH76Arg | 0.912 | 0.05 | 3 |
| F-13 | F-12 | LeuL46Val TyrL49Ser | 1.050 | 0.16 | 3 |
| F-14 | F-13 | *Leu**H71Arg* | 0.472 | 0.06 | 3 |
| F-15 | F-13 | *Lys**H73Asn* | 0.868 | 0.32 | 3 |

[a]Murine residues are in bold; residue numbers are according to Kabat et al. (1991).
Standard text indicates a change from a human framework residue to mouse.
Italic text indicates a change from a mouse framework residue to human.
Fab binding to IFN-α was assayed by ELISA and results are provided as OD$_{450nm}$ at 10 µg/ml.
SD, standard deviation; n, number of experimental replicates.

Previous humanizations (Xiang et al., *J. Mol. Biol.* 253: 385-390 [1995]; Werther et al., [1996] supra) as well as studies of F(ab)-antigen crystal structures (Chothia et al., [1989] supra; Tramontano et al., *J. Mol. Biol.* 215: 175-182 [1990]) have shown that residues H71 and H73 can have a profound effect on binding, possibly by influencing the conformations of CDR-H1 and CDR-H2. Changing the human residues at positions H71 and H73 to their murine counterparts improved binding only slightly (version F-2, Table 3). Further simultaneous changes at positions H67, H69 and H78 (version F-3) followed by changes ArgH94Ser (version F-4) and AlaH24Thr (version F-5) significantly improved binding (Table 3). Since positions H67, H69 and H78 had been changed simultaneously, each was individually altered back to the human consensus framework residue; versions F-7, F-8, F-9, and F-10 show that the human residue is preferred at position H67, position H69 does not show any preference for the human or murine residue, and the murine residue is preferred at position H78.

We have found during previous humanizations that residues in a framework loop, FR-3 (Kabat et al., (1991) supra), adjacent to CDR-H1 and CDR-H2 can affect binding (Eigenbrot et al., (1994) supra). Accordingly, two residues in this loop were changed to their murine counterparts: LysH75 to murine Ser (version F-11) and AsnH76 to murine Arg (version F-12). Only the AsnH76Arg change effected an improvement in binding (Table 3).

Inspection of the models of the murine and humanized F(ab)s suggested that residue L46, buried at the VL-VH interface and interacting with CDR-H3, might also play a role either in determining the conformation of CDR-H3 and/or affecting the interactions between the VL and VH domains. Similarly, L49 position which is adjacent to CDR-L2 differs between the human consensus (Tyr) and the 9F3 (Ser) sequence. Therefore, LeuL46Val and TyrL49Ser residues were simultaneously substituted, which resulted in a variant (F-13) with further improvement in the binding (Table 3). Based on its best binding among all the variants generated, F-13 was chosen as the final humanized version.

A humanized recombinant anti-IFN-α monoclonal antibody (V13IgG2) was generated by fusing VH and VL domains derived from F-13 to human IgG2 CH1-Fc and human CL domains respectively. The $K_{ON}$ rates and $K_D$ values of V13IgG2 were then compared with a chimeric IgG2 or murine 9F3. BIACore™ measurement of V13IgG2 and chimeric IgG2 binding to immobilized IFN-α showed that their $K_{ON}$ rates were similar (Table 4). Affinity measurement using Kinexa™ technology showed that the affinity of V13IgG2 for IFNα was reduced by 2-fold compared to the parental murine 9F3 antibody (Table 4).

TABLE 4

BIACore ™ and Kinexa ™ Data for Anti-IFNα Antibodies

| Antibody[a] | $K_{on}$ (µM/sec) | Kd (nM)[b] | Method |
|---|---|---|---|
| | | 0.14 | BIACore ™ |
| ChIgG2 | 3.9 | | BIACore ™ |
| V13IgG2 | 3.3 | | BIACore ™ |
| V13Fab | | 4.1 | BIACore ™ |

| Antibody[a] | $K_D$(pM) | | |
|---|---|---|---|
| murine 9F3 | 1.5 | | Kinexa ™ |
| V13Fab | 3.4 | | Kinexa ™ |

[a]V13IgG2 is F-13 VH domain joined to human IgG2 CH1-Fc and F-13 VL domain joined to a human CL domain; ChIgG2 is mouse 9F3 VH domain joined to human IgG2 CH1-Fc and mouse 9F3 VL domain joined to human CL domain.
[b]Koff/Kon.

Deposit of Material

The following materials have been deposited with the American Type Culture Collection, 10801 University Blvd., Manassas, Va. 20110-2209, USA (ATCC):

| Material | ATCC Dep. No. | Deposit Date |
|---|---|---|
| 1. A hybridoma cell line secreting 9F3 murine anti-IFN-α monoclonal antibodies (Id. Ref.: 9F3.18.5) | PTA-2917 | Jan. 18, 2001 |
| 2. pRK-based vector for the expression of heavy chain of chimeric CH8-2 full-length IgG (Id. Ref.: XAIFN-ChHpDR2) | PTA-2883 | Jan. 9, 2001 |
| 3. pRK-based vector for the expression of light chain of chimeric CH8-2 full-length IgG (Id. Ref.: XAIFN-ChLpDR1) | PTA-2880 | Jan. 9, 2001 |
| 4. pRK-based vector for the expression of heavy chain of humanized V13 full-length IgG$_2$ (Id. Ref.: VHV30-IgG2) | PTA-2881 | Jan. 9, 2001 |
| 5. pRK-based vector for the expression of light chain of humanized V13 full-length IgG$_2$ (Id. Ref.: VLV30-IgG) | PTA-2882 | Jan. 9, 2001 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 C.F.R. §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A method for the treatment of a disease or condition associated with the increased expression of IFN-α in a patient, comprising administering to said patient an effective amount of an anti-IFN-α antibody which binds to and neutralizes a biological activity of at least IFN-α subtypes IFN-α1, IFN-α2, IFN-α4, IFN-α5, IFN-α8, IFNα10, and IFN-α21.

2. The method of claim 1 wherein said patient is a mammalian patient.

3. The method of claim 2 wherein said patient is human.

4. The method of claim 3 wherein said disease is an autoimmune disease.

5. The method of claim 1 wherein said disease is selected from the group consisting of insulin-dependent diabetes mellitus (IDDM); systemic lupus erythematosus (SLE); and autoimmune thyroiditis.

6. The method of claim 1 wherein the antibody is a humanized antibody.

7. The method of claim 1 wherein the antibody is a humanized anti-human IFN-α monoclonal antibody comprising a light chain variable domain of SEQ ID NO:3 and a heavy chain variable domain of SEQ ID NO:5.

8. The method of claim 1 wherein the antibody binds essentially the same IFN-α epitope as the anti-IFN-α antibody produced by the hybridoma cell line deposited with ATCC on Jan. 18, 2001 and having accession No. PTA-2917.

9. The method of claim 1 wherein the antibody is of the IgG class.

10. The method of claim 9 wherein the antibody has an $IgG_1$, $IgG_2$, $IgG_3$, or $IgG_4$ isotype.

11. The method of claim 1 wherein the antibody is an antibody fragment.

12. The method of claim 11 wherein the antibody is a Fab fragment.

13. The method of claim 11 wherein the antibody is a $F(ab')_2$ fragment.

14. The method of claim 11 wherein the antibody is a Fab' fragment.

15. The method of claim 1 wherein the antibody is an antibody or antigen binding fragment that comprises a heavy chain variable domain and a light chain variable domain, wherein the light chain variable domain comprises the following CDR's:
  (a) L1 of the formula RASQSVSTSSYSYMH (SEQ ID NO: 7);
  (b) L2 of the formula YASNLES (SEQ ID NO: 8); and
  (c) L3 of the formula QHSWGIPRTF (SEQ ID NO: 9)
and wherein the antibody or antigen binding fragment specifically binds to at least IFN-α subtypes IFN-α1, IFN-α2, IFN-α4, IFN-α5, IFN-α8, IFN-α10, and IFN-α21.

16. The method of claim 15 wherein the antigen binding fragment is a Fab.

17. The method of claim 1 wherein the antibody is an antibody or antigen binding fragment that comprises a heavy chain variable domain and a light chain variable domain, wherein the heavy chain variable domain comprises, the following CDR's:
  (a) H1 of the formula GYTFTEYIIH (SEQ ID NO: 10);
  (b) H2 of the formula SINPDYDITNYNQRFKG (SEQ ID NO: 11); and
  (c) H3 of the formula WISDFFDY (SEQ ID NO: 12)
and wherein the antibody or antigen binding fragment specifically binds to at least IFN-α subtypes IFN-α1, IFN-α2, IFN-α4, IFN-α5, IFN-α8, IFN-α10, and IFN-α21.

18. The method of claim 17 wherein the antigen binding fragment is a Fab.

19. The method of claim 1 wherein the antibody comprises: (A) at least one light chain or an antigen binding fragment thereof, comprising the following CDR's:
  (a) L1 of the formula RASQSVSTSSYSYMH (SEQ ID NO: 7);
  (b) L2 of the formula YASNLES (SEQ ID NO: 8); and
  (c) L3 of the formula QHSWGIPRTF (SEQ ID NO: 9); and
(B) at least one heavy chain or an antigen binding fragment thereof, comprising the following CDR's:
  (a) H1 of the formula GYTFTEYIIH (SEQ ID NO: 10);
  (b) H2 of the formula SINPDYDITNYNQRFKG (SEQ ID NO: 11); and
  (c) H3 of the formula WISDFFDY (SEQ ID NO: 12).

20. The method of claim 19 wherein the antigen binding fragment is a Fab.

21. The method of claim 5 wherein said disease is insulin-dependent diabetes mellitus (IDDM).

22. The method of claim 5 wherein said disease is systemic lupus erythematosus (SLE).

23. The method of claim 5 wherein said disease is autoimmune thyroiditis.

* * * * *

SEQUENCE LISTING

```
<160> NUMBER OF SEQ ID NOS: 14

<210> SEQ ID NO 1
<211> LENGTH: 114
<212> TYPE: PRT
<213> ORGANISM: Murine

<400> SEQUENCE: 1

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Val Leu Ile Ser Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Gly Asp Thr Ala Thr Tyr Phe Cys Gln His Ser Trp
                85                  90                  95

Gly Ile Pro Arg Thr Phe Gly Ala Gly Thr Lys Leu Glu Leu Arg Arg
            100                 105                 110

Ala Val

<210> SEQ ID NO 2
<211> LENGTH: 119
<212> TYPE: PRT
<213> ORGANISM: Murine

<400> SEQUENCE: 2

Glu Val Gln Leu Gln Gln Ser Gly Pro Glu Leu Val Lys Pro Gly Ala
 1               5                  10                  15

Ser Val Lys Ile Ser Cys Lys Thr Ser Gly Tyr Thr Phe Thr Glu Tyr
            20                  25                  30

Ile Ile His Trp Val Lys Gln Gly His Gly Arg Ser Leu Glu Trp Ile
        35                  40                  45

Gly Ser Ile Asn Pro Asp Tyr Asp Ile Thr Asn Tyr Asn Gln Arg Phe
    50                  55                  60

Lys Gly Lys Ala Thr Leu Thr Leu Asp Lys Ser Ser Arg Thr Ala Tyr
```

```
                65                  70                  75                  80
Leu Glu Leu Arg Ser Leu Thr Ser Glu Asp Ser Ala Val Tyr Tyr Cys
                        85                  90                  95

Ala Ser Trp Ile Ser Asp Phe Phe Asp Tyr Trp Gly Gln Gly Thr Thr
                        100                 105                 110

Leu Met Val Ser Ala Ala Ser
        115

<210> SEQ ID NO 3
<211> LENGTH: 114
<212> TYPE: PRT
<213> ORGANISM: Artificial Sequence
<220> FEATURE:
<223> OTHER INFORMATION: This sequence represents a humanized chimeric
      antibody comprising human and non-human sequences.

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Thr Ser
                20                  25                  30

Ser Tyr Ser Tyr Met His Trp Tyr Gln Gln Lys Pro Gly Lys Ala Pro
        35                  40                  45

Lys Val Leu Ile Ser Tyr Ala Ser Asn Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Trp
                85                  90                  95

Gly Ile Pro Arg Thr Phe Gly Gln Gly Thr Lys Val Glu Ile Lys Arg
                100                 105                 110

Thr Val

<210> SEQ ID NO 4
<211> LENGTH: 110
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
                20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys Arg Thr Val
                100                 105                 110

<210> SEQ ID NO 5
<211> LENGTH: 119
<212> TYPE: PRT
```

<213> ORGANISM: Artificial Sequence
<220> FEATURE:
<223> OTHER INFORMATION: This sequence represents a humanized chimeric
      antibody comprising human and non-human sequences.

<400> SEQUENCE: 5

Glu Val Gln Leu Val Glu Ser Gly Gly Gly Leu Val Gln Pro Gly Gly
 1               5                  10                  15

Ser Leu Arg Leu Ser Cys Ala Thr Ser Gly Tyr Thr Phe Thr Glu Tyr
            20                  25                  30

Ile Ile His Trp Val Arg Gln Ala Pro Gly Lys Gly Leu Glu Trp Val
        35                  40                  45

Ala Ser Ile Asn Pro Asp Tyr Asp Ile Thr Asn Tyr Asn Gln Arg Phe
    50                  55                  60

Lys Gly Arg Phe Thr Ile Ser Leu Asp Lys Ser Lys Arg Thr Ala Tyr
65                  70                  75                  80

Leu Gln Met Asn Ser Leu Arg Ala Glu Asp Thr Ala Val Tyr Tyr Cys
                85                  90                  95

Ala Ser Trp Ile Ser Asp Phe Phe Asp Tyr Trp Gly Gln Gly Thr Leu
            100                 105                 110

Val Thr Val Ser Ser Ala Ser
        115

<210> SEQ ID NO 6
<211> LENGTH: 119
<212> TYPE: PRT
<213> ORGANISM: Homo sapiens

<400> SEQUENCE: 6

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Val Ile Ser Gly Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Val Gly Tyr Tyr Asp Tyr Trp Gly Gln Gly Thr Leu
            100                 105                 110

Val Thr Val Ser Ser Ala Ser
        115

<210> SEQ ID NO 7
<211> LENGTH: 15
<212> TYPE: PRT
<213> ORGANISM: Homo sapiens

<400> SEQUENCE: 7

Arg Ala Ser Gln Ser Val Ser Thr Ser Ser Tyr Ser Tyr Met His
 1               5                  10                  15

<210> SEQ ID NO 8
<211> LENGTH: 7

```
<212> TYPE: PRT
<213> ORGANISM: Homo sapiens

<400> SEQUENCE: 8

Tyr Ala Ser Asn Leu Glu Ser
1               5

<210> SEQ ID NO 9
<211> LENGTH: 10
<212> TYPE: PRT
<213> ORGANISM: Homo sapiens

<400> SEQUENCE: 9

Gln His Ser Trp Gly Ile Pro Arg Thr Phe
1               5                   10

<210> SEQ ID NO 10
<211> LENGTH: 10
<212> TYPE: PRT
<213> ORGANISM: Homo sapiens

<400> SEQUENCE: 10

Gly Tyr Thr Phe Thr Glu Tyr Ile Ile His
1               5                   10

<210> SEQ ID NO 11
<211> LENGTH: 17
<212> TYPE: PRT
<213> ORGANISM: Homo sapiens

<400> SEQUENCE: 11

Ser Ile Asn Pro Asp Tyr Asp Ile Thr Asn Tyr Asn Gln Arg Phe Lys
1               5                   10                  15

Gly

<210> SEQ ID NO 12
<211> LENGTH: 8
<212> TYPE: PRT
<213> ORGANISM: Homo sapiens

<400> SEQUENCE: 12

Trp Ile Ser Asp Phe Phe Asp Tyr
1               5

<210> SEQ ID NO 13
<211> LENGTH: 30
<212> TYPE: DNA
<213> ORGANISM: Homo sapiens

<400> SEQUENCE: 13
gatcgggaaa gggaaaccga aactgaagcc                                    30

<210> SEQ ID NO 14
<211> LENGTH: 30
<212> TYPE: DNA
<213> ORGANISM: Homo sapiens

<400> SEQUENCE: 14
gatcggcttc agtttcggtt tccctttccc                                    30
```